United States Patent
Harris et al.

(10) Patent No.: US 9,980,716 B2
(45) Date of Patent: May 29, 2018

(54) METHODS AND DEVICES FOR CREATING TISSUE PLICATIONS

(71) Applicant: Ethicon LLC, Guaynabo, PR (US)

(72) Inventors: Jason L. Harris, Hamilton, OH (US); Kevin D. Felder, Cincinnati, OH (US); Justin W. Sherrill, Alpharetta, GA (US)

(73) Assignee: Ethicon LLC, Guaynabo, PR (US)

( * ) Notice: Subject to any disclaimer, the term of this patent is extended or adjusted under 35 U.S.C. 154(b) by 0 days. days.

(21) Appl. No.: 14/671,357

(22) Filed: Mar. 27, 2015

(65) Prior Publication Data
US 2015/0196293 A1    Jul. 16, 2015

Related U.S. Application Data

(63) Continuation of application No. 13/425,900, filed on Mar. 21, 2012, now Pat. No. 8,992,547.

(51) Int. Cl.
*A61B 17/29* (2006.01)
*A61B 17/04* (2006.01)
*A61B 17/00* (2006.01)

(52) U.S. Cl.
CPC ...... *A61B 17/0401* (2013.01); *A61B 17/0487* (2013.01); *A61B 17/29* (2013.01);
(Continued)

(58) Field of Classification Search
CPC . A61B 17/0401; A61B 17/0487; A61B 17/29; A61B 2017/0404;
(Continued)

(56) References Cited

U.S. PATENT DOCUMENTS

| 2,069,878 A | 2/1937 | Flood |
| 2,185,518 A | 1/1940 | Posnack |

(Continued)

FOREIGN PATENT DOCUMENTS

| CN | 86106345 A | 7/1987 |
| DE | 2348670 A1 | 4/1974 |

(Continued)

OTHER PUBLICATIONS

U.S. Appl. No. 12/975,685, entitled, "Endoluminal Fold Creation," filed Dec. 22, 2010.

(Continued)

*Primary Examiner* — Corrine McDermott
*Assistant Examiner* — Tin Nguyen
(74) *Attorney, Agent, or Firm* — Mintz Levin Cohn Ferris Glovsky and Popeo, P.C.

(57) ABSTRACT

Devices and methods for forming and securing a tissue plication are disclosed herein. In one aspect, a tissue manipulation device is described that includes a first jaw member pivotally coupled to a distal end of an elongate shaft and having an articulating portion located distal to the proximal end of the first jaw member. The device also includes a second jaw member pivotally coupled to the first jaw member such that the jaws move in a first plane, and a fastener delivery member attached to the second jaw member. The articulating portion of the first jaw member is configured to move the first and second jaw members between a straight configuration in which a longitudinal axis of the elongate shaft is contained within the first plane and an articulated configuration in which the longitudinal axis of the elongate shaft is transverse to the first plane.

15 Claims, 17 Drawing Sheets

(52) U.S. Cl.
CPC .............. *A61B 2017/00349* (2013.01); *A61B 2017/00818* (2013.01); *A61B 2017/0404* (2013.01); *A61B 2017/0409* (2013.01); *A61B 2017/0417* (2013.01); *A61B 2017/2905* (2013.01); *A61B 2017/2927* (2013.01)

(58) Field of Classification Search
CPC .. A61B 2017/2905; A61B 2017/00818; A61B 2017/0409; A61B 2017/2927; A61B 2017/00349; A61B 2017/0417
See application file for complete search history.

(56) References Cited

U.S. PATENT DOCUMENTS

| | | | |
|---|---|---|---|
| 3,193,165 A | 7/1965 | Akhalaya et al. |
| 3,470,834 A | 10/1969 | Bone |
| 3,552,626 A | 1/1971 | Astafiev et al. |
| 3,638,847 A | 2/1972 | Noiles et al. |
| 3,694,819 A | 10/1972 | Meyer |
| 3,740,994 A | 6/1973 | De Carlo, Jr. |
| 3,802,438 A | 4/1974 | Wolvek |
| 3,819,100 A | 6/1974 | Noiles et al. |
| 3,890,970 A | 6/1975 | Gullen |
| 3,910,281 A | 10/1975 | Kletschka et al. |
| 3,990,619 A | 11/1976 | Russell |
| 4,006,747 A | 2/1977 | Kronenthal et al. |
| 4,022,191 A | 5/1977 | Jamshidi |
| 4,086,926 A | 5/1978 | Green et al. |
| 4,130,647 A | 12/1978 | Taylor |
| 4,216,777 A | 8/1980 | Pridemore |
| 4,235,238 A | 11/1980 | Ogiu et al. |
| 4,250,887 A | 2/1981 | Dardik et al. |
| 4,289,133 A | 9/1981 | Rothfuss |
| 4,331,276 A | 5/1982 | Bourque |
| 4,396,139 A | 8/1983 | Hall et al. |
| 4,407,286 A | 10/1983 | Noiles et al. |
| 4,430,997 A | 2/1984 | DiGiovanni et al. |
| 4,456,161 A | 6/1984 | Russell |
| 4,485,817 A | 12/1984 | Swiggett |
| 4,489,875 A | 12/1984 | Crawford et al. |
| 4,505,273 A | 3/1985 | Braun et al. |
| 4,509,518 A | 4/1985 | McGarry et al. |
| 4,522,207 A | 6/1985 | Klieman et al. |
| 4,624,254 A | 11/1986 | McGarry et al. |
| 4,648,542 A | 3/1987 | Fox et al. |
| 4,662,373 A | 5/1987 | Montgomery et al. |
| 4,669,473 A | 6/1987 | Richards et al. |
| 4,669,647 A | 6/1987 | Storace |
| 4,671,445 A | 6/1987 | Barker et al. |
| 4,700,703 A | 10/1987 | Resnick et al. |
| 4,705,040 A | 11/1987 | Mueller et al. |
| 4,741,330 A | 5/1988 | Hayhurst |
| 4,750,492 A | 6/1988 | Jacobs |
| 4,791,937 A | 12/1988 | Wang |
| 4,805,628 A | 2/1989 | Fry et al. |
| 4,841,888 A | 6/1989 | Mills et al. |
| 4,850,355 A | 7/1989 | Brooks et al. |
| 4,869,259 A | 9/1989 | Elkins |
| 4,874,122 A | 10/1989 | Froelich et al. |
| 4,899,745 A | 2/1990 | Laboureau et al. |
| 5,015,249 A | 5/1991 | Nakao et al. |
| 5,032,127 A | 7/1991 | Frazee et al. |
| 5,037,021 A | 8/1991 | Mills et al. |
| 5,041,129 A | 8/1991 | Hayhurst et al. |
| 5,046,513 A | 9/1991 | Gatturna et al. |
| 5,078,731 A | 1/1992 | Hayhurst |
| 5,080,663 A | 1/1992 | Mills et al. |
| 5,081,997 A | 1/1992 | Bosley, Jr. et al. |
| 5,123,914 A | 6/1992 | Cope |
| RE34,021 E | 8/1992 | Mueller et al. |
| 5,156,609 A | 10/1992 | Nakao et al. |
| 5,158,567 A | 10/1992 | Green |
| 5,171,251 A | 12/1992 | Bregen et al. |
| 5,217,486 A | 6/1993 | Rice et al. |
| 5,242,457 A | 9/1993 | Akopov et al. |
| 5,258,000 A | 11/1993 | Gianturco |
| 5,258,015 A | 11/1993 | Li et al. |
| 5,268,001 A | 12/1993 | Nicholson et al. |
| 5,269,809 A | 12/1993 | Hayhurst et al. |
| 5,282,832 A | 2/1994 | Toso et al. |
| 5,307,924 A | 5/1994 | Manosalva et al. |
| 5,312,023 A | 5/1994 | Green et al. |
| 5,312,024 A | 5/1994 | Grant et al. |
| 5,320,630 A | 6/1994 | Ahmed |
| 5,330,442 A | 7/1994 | Green et al. |
| 5,333,772 A | 8/1994 | Rothfuss et al. |
| 5,341,823 A | 8/1994 | Manosalva et al. |
| 5,350,400 A | 9/1994 | Esposito et al. |
| 5,354,298 A | 10/1994 | Lee et al. |
| 5,356,413 A | 10/1994 | Martins et al. |
| 5,366,459 A | 11/1994 | Yoon |
| 5,368,599 A | 11/1994 | Hirsch et al. |
| 5,376,101 A | 12/1994 | Green et al. |
| 5,383,905 A | 1/1995 | Golds et al. |
| 5,392,978 A | 2/1995 | Velez et al. |
| 5,403,326 A | 4/1995 | Harrison et al. |
| 5,403,348 A | 4/1995 | Bonutti |
| 5,405,354 A | 4/1995 | Sarrett |
| 5,409,499 A | 4/1995 | Yi |
| 5,413,584 A | 5/1995 | Schulze |
| 5,431,666 A | 7/1995 | Sauer et al. |
| 5,437,680 A | 8/1995 | Yoon |
| 5,439,468 A | 8/1995 | Schulze et al. |
| 5,462,558 A | 10/1995 | Kolesa et al. |
| 5,462,559 A | 10/1995 | Ahmed |
| 5,464,425 A | 11/1995 | Skiba |
| 5,465,567 A | 11/1995 | Schmolke et al. |
| 5,465,894 A | 11/1995 | Clark et al. |
| 5,465,895 A | 11/1995 | Knodel et al. |
| 5,470,337 A | 11/1995 | Moss |
| 5,472,452 A | 12/1995 | Trott |
| 5,474,572 A | 12/1995 | Hayhurst |
| 5,484,095 A | 1/1996 | Green et al. |
| 5,484,451 A | 1/1996 | Akopov et al. |
| 5,486,197 A | 1/1996 | Le et al. |
| 5,514,159 A | 5/1996 | Matula et al. |
| 5,520,702 A | 5/1996 | Sauer et al. |
| 5,522,843 A | 6/1996 | Zang |
| 5,531,678 A | 7/1996 | Tomba et al. |
| 5,531,699 A | 7/1996 | Tomba et al. |
| 5,540,704 A | 7/1996 | Gordon et al. |
| 5,544,802 A | 8/1996 | Crainich |
| 5,545,141 A | 8/1996 | Eld |
| 5,549,630 A | 8/1996 | Bonutti |
| 5,562,686 A | 10/1996 | Sauer et al. |
| 5,564,615 A | 10/1996 | Bishop et al. |
| 5,584,861 A | 12/1996 | Swain et al. |
| 5,584,862 A | 12/1996 | Bonutti |
| 5,591,180 A | 1/1997 | Hinchliffe |
| 5,591,202 A | 1/1997 | Slater et al. |
| 5,618,314 A | 4/1997 | Harwin et al. |
| 5,626,585 A | 5/1997 | Mittelstadt et al. |
| 5,626,614 A | 5/1997 | Hart |
| 5,630,540 A | 5/1997 | Blewell |
| 5,630,824 A | 5/1997 | Hart |
| 5,643,289 A | 7/1997 | Sauer et al. |
| 5,643,321 A | 7/1997 | McDevitt |
| 5,645,567 A | 7/1997 | Crainich |
| 5,649,963 A | 7/1997 | McDevitt |
| 5,662,683 A | 9/1997 | Kay |
| 5,669,917 A | 9/1997 | Sauer et al. |
| 5,673,841 A | 10/1997 | Schulze et al. |
| 5,681,344 A | 10/1997 | Kelly |
| 5,681,351 A | 10/1997 | Jamiolkowski et al. |
| 5,683,418 A | 11/1997 | Luscombe et al. |
| 5,690,655 A | 11/1997 | Hart et al. |
| 5,692,668 A | 12/1997 | Schulze et al. |
| 5,695,504 A | 12/1997 | Gifford, III et al. |
| 5,715,987 A | 2/1998 | Kelley et al. |
| 5,725,529 A | 3/1998 | Nicholson et al. |
| 5,725,554 A | 3/1998 | Simon et al. |
| 5,725,556 A | 3/1998 | Moser et al. |
| 5,728,116 A | 3/1998 | Rosenman |

(56) References Cited

U.S. PATENT DOCUMENTS

| | | |
|---|---|---|
| 5,728,119 A | 3/1998 | Smith et al. |
| 5,732,871 A | 3/1998 | Clark et al. |
| 5,733,306 A | 3/1998 | Bonutti |
| 5,733,325 A | 3/1998 | Robinson et al. |
| 5,735,875 A | 4/1998 | Bonutti et al. |
| 5,741,277 A | 4/1998 | Gordon et al. |
| 5,755,730 A | 5/1998 | Swain et al. |
| 5,762,255 A | 6/1998 | Chrisman et al. |
| 5,766,183 A | 6/1998 | Sauer |
| 5,792,153 A | 8/1998 | Swain et al. |
| 5,800,445 A | 9/1998 | Ratcliff et al. |
| 5,814,071 A | 9/1998 | McDevitt et al. |
| 5,826,776 A | 10/1998 | Schulze et al. |
| 5,829,662 A | 11/1998 | Allen et al. |
| 5,885,294 A | 3/1999 | Pedlick et al. |
| 5,897,563 A | 4/1999 | Yoon et al. |
| 5,897,564 A | 4/1999 | Schulze et al. |
| 5,899,921 A | 5/1999 | Caspari et al. |
| 5,902,321 A | 5/1999 | Caspari et al. |
| 5,904,696 A | 5/1999 | Rosenman |
| 5,910,105 A | 6/1999 | Swain et al. |
| RE36,289 E | 8/1999 | Le et al. |
| 5,931,844 A | 8/1999 | Thompson et al. |
| 5,935,129 A | 8/1999 | McDevitt et al. |
| 5,941,900 A | 8/1999 | Bonutti |
| 5,944,724 A | 8/1999 | Lizardi |
| 5,948,000 A | 9/1999 | Larsen et al. |
| 5,954,747 A | 9/1999 | Clark |
| 5,961,538 A | 10/1999 | Pedlick et al. |
| 5,980,558 A | 11/1999 | Wiley |
| 6,010,515 A | 1/2000 | Swain et al. |
| 6,010,525 A | 1/2000 | Bonutti et al. |
| 6,036,694 A | 3/2000 | Goble et al. |
| 6,036,701 A | 3/2000 | Rosenman |
| 6,044,847 A | 4/2000 | Carter et al. |
| 6,045,574 A | 4/2000 | Thal |
| 6,051,247 A | 4/2000 | Hench et al. |
| 6,056,751 A | 5/2000 | Fenton, Jr. |
| 6,066,146 A | 5/2000 | Carroll et al. |
| 6,068,648 A | 5/2000 | Cole et al. |
| 6,071,289 A | 6/2000 | Stefanchik et al. |
| 6,077,292 A | 6/2000 | Bonutti |
| 6,086,608 A | 7/2000 | Ek et al. |
| 6,099,547 A | 8/2000 | Gellman et al. |
| 6,102,922 A | 8/2000 | Jakobsson et al. |
| 6,143,017 A | 11/2000 | Thal |
| 6,146,406 A | 11/2000 | Shluzas et al. |
| 6,149,669 A | 11/2000 | Li |
| 6,152,935 A | 11/2000 | Kammerer et al. |
| 6,159,234 A | 12/2000 | Bonutti et al. |
| 6,165,204 A | 12/2000 | Levinson et al. |
| 6,200,329 B1 | 3/2001 | Fung et al. |
| 6,206,895 B1 | 3/2001 | Levinson |
| 6,228,098 B1 | 5/2001 | Kayan et al. |
| 6,231,561 B1 | 5/2001 | Frazier et al. |
| 6,231,581 B1 | 5/2001 | Shank et al. |
| 6,231,592 B1 | 5/2001 | Bonutti et al. |
| 6,241,747 B1 | 6/2001 | Ruff |
| 6,245,082 B1 | 6/2001 | Gellman et al. |
| 6,264,086 B1 | 7/2001 | McGuckin, Jr. |
| 6,293,961 B2 | 7/2001 | Schwartz |
| 6,269,997 B1 | 8/2001 | Balazs et al. |
| 6,277,131 B1 | 8/2001 | Kalikow |
| 6,287,325 B1 | 9/2001 | Bonutti |
| 6,302,886 B1 | 10/2001 | McDevitt et al. |
| 6,306,149 B1 | 10/2001 | Meade |
| 6,306,159 B1 | 10/2001 | Schwartz |
| 6,319,271 B1 | 11/2001 | Schwartz |
| 6,330,964 B1 | 12/2001 | Kayan et al. |
| 6,352,541 B1 | 3/2002 | Kienzle et al. |
| 6,368,334 B1 | 4/2002 | Sauer |
| 6,372,245 B1 | 4/2002 | Bowman et al. |
| 6,405,733 B1 | 6/2002 | Fogarty et al. |
| 6,436,088 B2 | 8/2002 | Frazier et al. |
| 6,440,154 B2 | 8/2002 | Gellman et al. |
| 6,447,524 B1 | 9/2002 | Knodel et al. |
| 6,450,391 B1 | 9/2002 | Kayan et al. |
| 6,453,780 B2 | 9/2002 | Habermehl |
| 6,468,228 B1 | 10/2002 | Topel et al. |
| 6,468,293 B2 | 10/2002 | Bonutti et al. |
| 6,478,791 B1 | 11/2002 | Carter et al. |
| 6,494,888 B1 | 12/2002 | Laufer et al. |
| 6,500,184 B1 | 12/2002 | Chan et al. |
| 6,500,195 B2 | 12/2002 | Bonutti |
| 6,506,190 B1 | 1/2003 | Walshe |
| 6,506,196 B1 | 1/2003 | Laufer |
| 6,524,328 B2 | 2/2003 | Levinson |
| 6,527,794 B1 | 3/2003 | McDevitt et al. |
| 6,527,795 B1 | 3/2003 | Lizardi |
| 6,530,933 B1 | 3/2003 | Yeung et al. |
| 6,533,796 B1 | 3/2003 | Sauer et al. |
| 6,551,333 B2 | 4/2003 | Kuhns et al. |
| 6,558,400 B2 | 5/2003 | Deem et al. |
| 6,561,969 B2 | 5/2003 | Frazier et al. |
| 6,564,806 B1 | 5/2003 | Fogarty et al. |
| 6,566,484 B2 | 5/2003 | Gharda et al. |
| 6,569,187 B1 | 5/2003 | Bonutti et al. |
| 6,572,626 B1 | 6/2003 | Knodel et al. |
| 6,572,629 B2 | 6/2003 | Kalloo et al. |
| 6,575,987 B2 | 6/2003 | Gellman et al. |
| 6,582,453 B1 | 6/2003 | Tran et al. |
| 6,592,593 B1 | 7/2003 | Parodi et al. |
| 6,599,311 B1 | 7/2003 | Biggs et al. |
| 6,626,899 B2 | 9/2003 | Houser et al. |
| 6,652,561 B1 | 11/2003 | Tran |
| 6,652,562 B2 | 11/2003 | Collier et al. |
| 6,660,023 B2 | 12/2003 | McDevitt et al. |
| 6,663,639 B1 | 12/2003 | Laufer et al. |
| 6,669,687 B1 | 12/2003 | Saadat |
| 6,679,889 B1 | 1/2004 | West, Jr. et al. |
| 6,692,516 B2 | 2/2004 | West, Jr. et al. |
| 6,695,854 B1 | 2/2004 | Kayan et al. |
| 6,699,263 B2 | 3/2004 | Cope |
| 6,722,371 B1 | 4/2004 | Fogarty et al. |
| 6,726,705 B2 | 4/2004 | Peterson et al. |
| 6,733,531 B1 | 5/2004 | Trieu |
| 6,740,098 B2 | 5/2004 | Abrams et al. |
| 6,746,460 B2 | 6/2004 | Gannoe et al. |
| 6,767,356 B2 | 7/2004 | Kanner et al. |
| 6,769,590 B2 | 8/2004 | Vresh et al. |
| 6,773,440 B2 | 8/2004 | Gannoe et al. |
| 6,773,441 B1 | 8/2004 | Laufer et al. |
| 6,773,450 B2 | 8/2004 | Leung et al. |
| 6,780,198 B1 | 8/2004 | Gregoire et al. |
| 6,790,214 B2 | 9/2004 | Kraemer et al. |
| 6,800,081 B2 | 10/2004 | Parodi |
| 6,808,491 B2 | 10/2004 | Kortenbach et al. |
| 6,821,285 B2 | 11/2004 | Laufer et al. |
| 6,835,200 B2 | 12/2004 | Laufer et al. |
| 6,837,895 B2 | 1/2005 | Mayenberger |
| 6,881,816 B2 | 4/2005 | Gharda et al. |
| 6,884,248 B2 | 4/2005 | Bolduc et al. |
| 6,908,427 B2 | 6/2005 | Fleener et al. |
| 6,909,015 B2 | 6/2005 | Kemmish et al. |
| 6,915,937 B2 | 7/2005 | Lat et al. |
| 6,916,327 B2 | 7/2005 | Northrup, III et al. |
| 6,923,754 B2 | 8/2005 | Lubock |
| 6,932,835 B2 | 8/2005 | Bonutti et al. |
| 6,957,756 B2 | 10/2005 | Lat et al. |
| 6,960,217 B2 | 11/2005 | Bolduc |
| 6,966,919 B2 | 11/2005 | Sixto, Jr. et al. |
| 6,986,737 B2 | 1/2006 | Suzuki et al. |
| 6,986,775 B2 | 1/2006 | Morales et al. |
| 6,988,985 B2 | 1/2006 | Suzuki et al. |
| 6,991,643 B2 | 1/2006 | Saadat |
| 6,994,715 B2 | 2/2006 | Gannoe et al. |
| 6,997,931 B2 | 2/2006 | Sauer et al. |
| 6,997,932 B2 | 2/2006 | Dreyfuss et al. |
| 7,001,400 B1 | 2/2006 | Modesitt et al. |
| 7,001,410 B2 | 2/2006 | Fisher et al. |
| 7,008,419 B2 | 3/2006 | Shadduck |
| 7,016,735 B2 | 3/2006 | Imran et al. |
| 7,020,531 B1 | 3/2006 | Colliou et al. |
| 7,029,481 B1 | 4/2006 | Burdulis, Jr. et al. |

(56) References Cited

U.S. PATENT DOCUMENTS

| | | |
|---|---|---|
| 7,033,370 B2 | 4/2006 | Gordon et al. |
| 7,033,378 B2 | 4/2006 | Smith et al. |
| 7,033,380 B2 | 4/2006 | Schwartz et al. |
| 7,037,315 B2 | 5/2006 | Sancoff et al. |
| 7,041,111 B2 | 5/2006 | Chu |
| 7,044,934 B2 | 5/2006 | Mickley |
| 7,048,749 B2 | 5/2006 | Kortenbach et al. |
| 7,048,755 B2 | 5/2006 | Bonutti et al. |
| 7,056,330 B2 | 6/2006 | Gayton |
| 7,059,331 B2 | 6/2006 | Adams et al. |
| 7,059,509 B2 | 6/2006 | Brown |
| 7,063,715 B2 | 6/2006 | Onuki et al. |
| 7,083,629 B2 | 8/2006 | Weller et al. |
| 7,083,630 B2 | 8/2006 | DeVries et al. |
| 7,097,650 B2 | 8/2006 | Weller et al. |
| 7,112,214 B2 | 9/2006 | Peterson et al. |
| 7,153,314 B2 | 12/2006 | Laufer et al. |
| 7,160,312 B2 | 1/2007 | Saadat |
| 7,175,638 B2 | 2/2007 | Gannoe et al. |
| 7,175,648 B2 | 2/2007 | Nakao |
| 7,179,265 B2 | 2/2007 | Manetakis et al. |
| 7,214,233 B2 | 5/2007 | Gannoe et al. |
| 7,217,425 B2 | 5/2007 | Serhan et al. |
| 7,232,445 B2 | 6/2007 | Kortenbach et al. |
| 7,300,454 B2 | 11/2007 | Park et al. |
| 7,306,614 B2 | 12/2007 | Weller et al. |
| 7,320,692 B1 | 1/2008 | Bender et al. |
| 7,344,544 B2 | 3/2008 | Bender et al. |
| 7,347,863 B2 | 3/2008 | Rothe et al. |
| 7,361,180 B2 | 4/2008 | Saadat et al. |
| 7,364,060 B2 | 4/2008 | Milliman |
| 7,390,329 B2 | 6/2008 | Westra et al. |
| 7,407,076 B2 | 8/2008 | Racenet et al. |
| 7,416,554 B2 | 8/2008 | Lam et al. |
| 7,431,725 B2 | 10/2008 | Stack et al. |
| 7,458,978 B1 | 12/2008 | Bender et al. |
| 7,473,258 B2 | 1/2009 | Clauson et al. |
| 7,503,922 B2 | 3/2009 | Deem et al. |
| 7,506,791 B2 | 3/2009 | Omaits et al. |
| 7,513,408 B2 | 4/2009 | Shelton, IV et al. |
| 7,533,790 B1 | 5/2009 | Knodel et al. |
| 7,556,647 B2 | 7/2009 | Drews et al. |
| 7,618,426 B2 | 11/2009 | Ewers et al. |
| 7,641,671 B2 | 1/2010 | Crainich |
| 7,708,181 B2 | 5/2010 | Cole et al. |
| 7,736,374 B2 | 6/2010 | Vaughan et al. |
| 7,741,520 B2 | 6/2010 | Brueggemeier et al. |
| 7,744,613 B2 | 6/2010 | Ewers et al. |
| 7,753,250 B2 | 7/2010 | Clauson et al. |
| 7,753,870 B2 | 7/2010 | Demarais et al. |
| 7,757,924 B2 | 7/2010 | Gerbi et al. |
| 7,794,475 B2 | 9/2010 | Hess et al. |
| 7,832,408 B2 | 11/2010 | Shelton, IV et al. |
| 7,887,553 B2 | 2/2011 | Lehman et al. |
| 7,914,543 B2 | 3/2011 | Roth et al. |
| 7,934,631 B2 | 5/2011 | Balbierz et al. |
| 7,954,684 B2 | 6/2011 | Boudreaux |
| 8,006,167 B2 | 8/2011 | Lapstun et al. |
| 8,007,505 B2 | 8/2011 | Weller et al. |
| 8,057,490 B2 | 11/2011 | Harris et al. |
| 8,066,720 B2 | 11/2011 | Knodel et al. |
| 8,092,378 B2 | 1/2012 | Roth et al. |
| 8,142,450 B2 | 3/2012 | Harris et al. |
| 8,216,236 B2 | 7/2012 | Heinrich et al. |
| 8,257,365 B2 | 9/2012 | Demarais et al. |
| 8,342,376 B2 | 1/2013 | Surti |
| 8,439,244 B2 | 5/2013 | Holcomb et al. |
| 8,449,560 B2 | 5/2013 | Roth et al. |
| 8,469,252 B2 | 6/2013 | Holcomb et al. |
| 8,469,977 B2 | 6/2013 | Balbierz et al. |
| 8,602,286 B2 | 12/2013 | Crainich et al. |
| 8,728,119 B2 | 5/2014 | Cummins |
| 8,801,732 B2 | 8/2014 | Harris et al. |
| 8,858,579 B2 | 10/2014 | Suyker et al. |
| 8,992,547 B2 | 3/2015 | Harris et al. |
| 2001/0010005 A1 | 7/2001 | Kammerer et al. |
| 2001/0044656 A1 | 11/2001 | Williamson et al. |
| 2002/0010390 A1 | 1/2002 | Guice et al. |
| 2002/0028980 A1 | 3/2002 | Thierfelder et al. |
| 2002/0059938 A1 | 5/2002 | Fogarty et al. |
| 2002/0077661 A1 | 6/2002 | Saadat |
| 2002/0111653 A1 | 8/2002 | Foerster |
| 2002/0116070 A1 | 8/2002 | Amara et al. |
| 2002/0123758 A1 | 9/2002 | Bachman et al. |
| 2002/0128684 A1 | 9/2002 | Foerster |
| 2002/0156150 A1 | 10/2002 | Williams et al. |
| 2002/0169465 A1 | 11/2002 | Bowman et al. |
| 2002/0188305 A1 | 12/2002 | Foerster et al. |
| 2002/0189622 A1 | 12/2002 | Cauthen et al. |
| 2003/0004578 A1 | 1/2003 | Brown et al. |
| 2003/0018358 A1 | 1/2003 | Saadat |
| 2003/0023268 A1 | 1/2003 | Lizardi |
| 2003/0069593 A1 | 4/2003 | Tremulis et al. |
| 2003/0093117 A1 | 5/2003 | Saadat |
| 2003/0097150 A1 | 5/2003 | Fallin et al. |
| 2003/0109900 A1 | 6/2003 | Martinek |
| 2003/0125767 A1 | 7/2003 | Collier et al. |
| 2003/0158581 A1 | 8/2003 | Levinson |
| 2003/0163143 A1 | 8/2003 | Wakabayashi |
| 2003/0163160 A1 | 8/2003 | O'Malley et al. |
| 2003/0171760 A1 | 9/2003 | Gambale |
| 2003/0181800 A1 | 9/2003 | Bonutti |
| 2003/0181926 A1 | 9/2003 | Dana et al. |
| 2003/0191497 A1 | 10/2003 | Cope |
| 2003/0216613 A1 | 11/2003 | Suzuki et al. |
| 2003/0220685 A1 | 11/2003 | Hlavka et al. |
| 2003/0233056 A1 | 12/2003 | Saadat et al. |
| 2003/0236535 A1 | 12/2003 | Onuki et al. |
| 2003/0236573 A1 | 12/2003 | Evans et al. |
| 2004/0010245 A1 | 1/2004 | Cerier et al. |
| 2004/0034371 A1 | 2/2004 | Lehman et al. |
| 2004/0049211 A1 | 3/2004 | Tremulis et al. |
| 2004/0059416 A1 | 3/2004 | Murray et al. |
| 2004/0073219 A1 | 4/2004 | Skiba et al. |
| 2004/0092892 A1 | 5/2004 | Kagan et al. |
| 2004/0093023 A1 | 5/2004 | Allen et al. |
| 2004/0093057 A1 | 5/2004 | Bolduc et al. |
| 2004/0097971 A1 | 5/2004 | Hughett |
| 2004/0098050 A1 | 5/2004 | Foerster et al. |
| 2004/0102809 A1 | 5/2004 | Anderson |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0133220 A1 | 7/2004 | Lashinski et al. |
| 2004/0133238 A1 | 7/2004 | Cerier |
| 2004/0138525 A1 | 7/2004 | Saadat et al. |
| 2004/0138529 A1 | 7/2004 | Wiltshire et al. |
| 2004/0144395 A1 | 7/2004 | Evans et al. |
| 2004/0147958 A1 | 7/2004 | Lam et al. |
| 2004/0153008 A1 | 8/2004 | Sharf et al. |
| 2004/0153103 A1 | 8/2004 | Schwartz et al. |
| 2004/0162568 A1 | 8/2004 | Saadat et al. |
| 2004/0167546 A1 | 8/2004 | Saadat et al. |
| 2004/0186514 A1 | 9/2004 | Swain et al. |
| 2004/0186566 A1 | 9/2004 | Hindrichs et al. |
| 2004/0193184 A1 | 9/2004 | Laufer et al. |
| 2004/0193190 A1 | 9/2004 | Liddicoat et al. |
| 2004/0193191 A1 | 9/2004 | Starksen et al. |
| 2004/0194790 A1 | 10/2004 | Laufer et al. |
| 2004/0199059 A1 | 10/2004 | Brauker et al. |
| 2004/0210243 A1 | 10/2004 | Gannoe et al. |
| 2004/0215216 A1 | 10/2004 | Gannoe et al. |
| 2004/0225183 A1 | 11/2004 | Michlitsch et al. |
| 2004/0225305 A1* | 11/2004 | Ewers ............... A61B 1/00135 606/153 |
| 2004/0243178 A1 | 12/2004 | Haut et al. |
| 2004/0243227 A1 | 12/2004 | Starksen et al. |
| 2004/0249367 A1 | 12/2004 | Saadat et al. |
| 2004/0249392 A1 | 12/2004 | Mikkaichi et al. |
| 2004/0254622 A1 | 12/2004 | Shadduck |
| 2004/0260344 A1 | 12/2004 | Lyons et al. |
| 2005/0019368 A1 | 1/2005 | Cook et al. |
| 2005/0033319 A1 | 2/2005 | Gambale et al. |
| 2005/0033328 A1 | 2/2005 | Laufer et al. |

(56) References Cited

U.S. PATENT DOCUMENTS

| | | |
|---|---|---|
| 2005/0033403 A1 | 2/2005 | Ward et al. |
| 2005/0038437 A1 | 2/2005 | McDevitt et al. |
| 2005/0049617 A1 | 3/2005 | Chatlynne et al. |
| 2005/0055052 A1 | 3/2005 | Lombardo et al. |
| 2005/0055087 A1 | 3/2005 | Starksen |
| 2005/0055089 A1 | 3/2005 | Macoviak et al. |
| 2005/0065397 A1 | 3/2005 | Saadat et al. |
| 2005/0065401 A1 | 3/2005 | Saadat et al. |
| 2005/0065536 A1 | 3/2005 | Ewers et al. |
| 2005/0070931 A1 | 3/2005 | Li et al. |
| 2005/0075653 A1 | 4/2005 | Saadat et al. |
| 2005/0075654 A1 | 4/2005 | Kelleher |
| 2005/0080454 A1 | 4/2005 | Drews et al. |
| 2005/0085830 A1 | 4/2005 | Lehman et al. |
| 2005/0085903 A1 | 4/2005 | Lau |
| 2005/0096673 A1 | 5/2005 | Stack et al. |
| 2005/0101977 A1 | 5/2005 | Gannoe et al. |
| 2005/0107663 A1 | 5/2005 | Saadat et al. |
| 2005/0113640 A1 | 5/2005 | Saadat et al. |
| 2005/0113851 A1 | 5/2005 | Swain et al. |
| 2005/0116009 A1 | 6/2005 | Milliman |
| 2005/0119735 A1 | 6/2005 | Spence et al. |
| 2005/0142163 A1 | 6/2005 | Hunter et al. |
| 2005/0143762 A1 | 6/2005 | Paraschac et al. |
| 2005/0165429 A1 | 7/2005 | Douglas et al. |
| 2005/0177176 A1 | 8/2005 | Gerbi et al. |
| 2005/0187565 A1 | 8/2005 | Baker et al. |
| 2005/0187567 A1 | 8/2005 | Baker et al. |
| 2005/0192599 A1 | 9/2005 | Demarais |
| 2005/0192601 A1 | 9/2005 | Demarais |
| 2005/0203488 A1 | 9/2005 | Michlitsch et al. |
| 2005/0203489 A1 | 9/2005 | Saadat et al. |
| 2005/0203500 A1 | 9/2005 | Saadat et al. |
| 2005/0203547 A1 | 9/2005 | Weller et al. |
| 2005/0203548 A1 | 9/2005 | Weller et al. |
| 2005/0215945 A1 | 9/2005 | Harris et al. |
| 2005/0222592 A1 | 10/2005 | Gannoe et al. |
| 2005/0222678 A1 | 10/2005 | Lashinski et al. |
| 2005/0228410 A1 | 10/2005 | Berreklouw |
| 2005/0234512 A1 | 10/2005 | Nakao |
| 2005/0245945 A1 | 11/2005 | Ewers et al. |
| 2005/0247320 A1 | 11/2005 | Stack et al. |
| 2005/0250980 A1 | 11/2005 | Swanstrom et al. |
| 2005/0250984 A1 | 11/2005 | Lam et al. |
| 2005/0250985 A1 | 11/2005 | Saadat et al. |
| 2005/0250986 A1 | 11/2005 | Rothe et al. |
| 2005/0250987 A1 | 11/2005 | Ewers et al. |
| 2005/0250988 A1 | 11/2005 | Ewers et al. |
| 2005/0251091 A1 | 11/2005 | Saadat et al. |
| 2005/0251157 A1 | 11/2005 | Saadat et al. |
| 2005/0251158 A1 | 11/2005 | Saadat et al. |
| 2005/0251159 A1 | 11/2005 | Ewers et al. |
| 2005/0251160 A1 | 11/2005 | Saadat et al. |
| 2005/0251161 A1 | 11/2005 | Saadat et al. |
| 2005/0251162 A1 | 11/2005 | Rothe et al. |
| 2005/0251165 A1 | 11/2005 | Vaughan et al. |
| 2005/0251166 A1 | 11/2005 | Vaughan et al. |
| 2005/0251177 A1 | 11/2005 | Saadat et al. |
| 2005/0251189 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0256531 A9 | 11/2005 | Bolduc et al. |
| 2005/0256533 A1 | 11/2005 | Roth et al. |
| 2005/0261708 A1 | 11/2005 | Pasricha et al. |
| 2005/0261709 A1 | 11/2005 | Sakamoto et al. |
| 2005/0261710 A1 | 11/2005 | Sakamoto et al. |
| 2005/0261712 A1 | 11/2005 | Balbierz et al. |
| 2005/0267495 A1 | 12/2005 | Ginn et al. |
| 2005/0267534 A1 | 12/2005 | Bonutti et al. |
| 2005/0273138 A1 | 12/2005 | To et al. |
| 2005/0277957 A1 | 12/2005 | Kuhns et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2005/0288688 A1 | 12/2005 | Sakamoto et al. |
| 2005/0288689 A1 | 12/2005 | Kammerer et al. |
| 2005/0288708 A1 | 12/2005 | Kammerer et al. |
| 2006/0004385 A1 | 1/2006 | Gellman et al. |
| 2006/0004409 A1 | 1/2006 | Nobis et al. |
| 2006/0004410 A1 | 1/2006 | Nobis et al. |
| 2006/0009789 A1 | 1/2006 | Gambale et al. |
| 2006/0009792 A1 | 1/2006 | Baker et al. |
| 2006/0015125 A1 | 1/2006 | Swain |
| 2006/0020162 A1 | 1/2006 | Whayne et al. |
| 2006/0020167 A1 | 1/2006 | Sitzmann |
| 2006/0020254 A1 | 1/2006 | Hoffmann |
| 2006/0020274 A1 | 1/2006 | Ewers et al. |
| 2006/0020276 A1 | 1/2006 | Saadat et al. |
| 2006/0020277 A1 | 1/2006 | Gostout et al. |
| 2006/0020278 A1 | 1/2006 | Burnett et al. |
| 2006/0025652 A1 | 2/2006 | Vargas |
| 2006/0025789 A1 | 2/2006 | Laufer et al. |
| 2006/0025819 A1 | 2/2006 | Nobis et al. |
| 2006/0030884 A1 | 2/2006 | Yeung et al. |
| 2006/0041263 A1 | 2/2006 | Chu et al. |
| 2006/0047289 A1 | 3/2006 | Fogel |
| 2006/0052801 A1 | 3/2006 | Dreyfuss et al. |
| 2006/0052824 A1 | 3/2006 | Ransick et al. |
| 2006/0052825 A1 | 3/2006 | Ransick et al. |
| 2006/0058582 A1 | 3/2006 | Maahs et al. |
| 2006/0060630 A1 | 3/2006 | Shelton et al. |
| 2006/0079914 A1 | 4/2006 | Modesitt et al. |
| 2006/0100643 A1 | 5/2006 | Laufer et al. |
| 2006/0106405 A1 | 5/2006 | Fann et al. |
| 2006/0135996 A1 | 6/2006 | Schwartz et al. |
| 2006/0151568 A1 | 7/2006 | Weller et al. |
| 2006/0157067 A1 | 7/2006 | Saadat et al. |
| 2006/0161185 A1 | 7/2006 | Saadat et al. |
| 2006/0178560 A1 | 8/2006 | Saadat et al. |
| 2006/0217749 A1 | 9/2006 | Wilson et al. |
| 2006/0271073 A1 | 11/2006 | Lam et al. |
| 2006/0271101 A1* | 11/2006 | Saadat ............... A61B 17/0469 606/205 |
| 2006/0276810 A1 | 12/2006 | Kelleher et al. |
| 2007/0016056 A1 | 1/2007 | Kerwin |
| 2007/0060932 A1 | 3/2007 | Stack et al. |
| 2007/0112364 A1 | 5/2007 | Gerbi et al. |
| 2007/0162056 A1 | 7/2007 | Gerbi et al. |
| 2007/0167960 A1 | 7/2007 | Roth et al. |
| 2007/0175488 A1 | 8/2007 | Cox et al. |
| 2007/0181138 A1 | 8/2007 | Gannoe et al. |
| 2007/0185504 A1 | 8/2007 | Manetakis et al. |
| 2007/0191871 A1 | 8/2007 | Baker et al. |
| 2007/0208360 A1 | 9/2007 | Demarais et al. |
| 2007/0219566 A1 | 9/2007 | Gambale |
| 2007/0219571 A1 | 9/2007 | Balbierz et al. |
| 2007/0225737 A1 | 9/2007 | Messerly et al. |
| 2007/0233161 A1 | 10/2007 | Weller et al. |
| 2007/0276432 A1 | 11/2007 | Stack et al. |
| 2008/0039879 A1 | 2/2008 | Chin et al. |
| 2008/0045598 A1 | 2/2008 | Brueggemeier et al. |
| 2008/0051823 A1 | 2/2008 | Makower et al. |
| 2008/0065122 A1 | 3/2008 | Stack et al. |
| 2008/0078805 A1 | 4/2008 | Omaits et al. |
| 2008/0082124 A1 | 4/2008 | Hess et al. |
| 2008/0086155 A1 | 4/2008 | Rothe et al. |
| 2008/0091079 A1 | 4/2008 | Roth et al. |
| 2008/0103357 A1 | 5/2008 | Zeiner et al. |
| 2008/0132925 A1 | 6/2008 | Demarais |
| 2008/0147112 A1 | 6/2008 | Sheets et al. |
| 2008/0172074 A1 | 7/2008 | Baker et al. |
| 2008/0177304 A1 | 7/2008 | Westra et al. |
| 2008/0190989 A1 | 8/2008 | Crews et al. |
| 2008/0207995 A1 | 8/2008 | Kortenbach et al. |
| 2008/0208214 A1 | 8/2008 | Sato et al. |
| 2008/0208216 A1 | 8/2008 | Cerier |
| 2008/0217376 A1 | 9/2008 | Clauson et al. |
| 2008/0228199 A1 | 9/2008 | Cropper et al. |
| 2008/0228203 A1 | 9/2008 | Bell et al. |

(56) References Cited

U.S. PATENT DOCUMENTS

| | | |
|---|---|---|
| 2008/0234703 A1 | 9/2008 | Cropper et al. |
| 2008/0234705 A1 | 9/2008 | Cropper et al. |
| 2008/0249561 A1 | 10/2008 | Stokes et al. |
| 2008/0249566 A1 | 10/2008 | Harris et al. |
| 2008/0294179 A1 | 11/2008 | Balbierz et al. |
| 2008/0314957 A1 | 12/2008 | Boudreaux |
| 2008/0319455 A1 | 12/2008 | Harris et al. |
| 2009/0024144 A1 | 1/2009 | Zeiner et al. |
| 2009/0024163 A1 | 1/2009 | Zeiner et al. |
| 2009/0072006 A1 | 3/2009 | Clauson et al. |
| 2009/0076055 A1 | 3/2009 | Czarnik |
| 2009/0112233 A1 | 4/2009 | Xiao |
| 2009/0112304 A1 | 4/2009 | Weadock et al. |
| 2009/0125040 A1 | 5/2009 | Hambly et al. |
| 2009/0134198 A1 | 5/2009 | Knodel et al. |
| 2009/0134199 A1 | 5/2009 | Heinrich et al. |
| 2009/0206127 A1 | 8/2009 | Danielson et al. |
| 2009/0275967 A1 | 11/2009 | Stokes et al. |
| 2009/0276055 A1 | 11/2009 | Harris et al. |
| 2009/0318936 A1 | 12/2009 | Harris et al. |
| 2009/0326578 A1 | 12/2009 | Ewers et al. |
| 2010/0082046 A1 | 4/2010 | Harris et al. |
| 2010/0116867 A1 | 5/2010 | Balbierz et al. |
| 2010/0137681 A1 | 6/2010 | Ewers et al. |
| 2010/0187283 A1 | 7/2010 | Crainich et al. |
| 2010/0187284 A1 | 7/2010 | Crainich et al. |
| 2010/0191255 A1 | 7/2010 | Crainich et al. |
| 2010/0191258 A1 | 7/2010 | Harris et al. |
| 2010/0191282 A1 | 7/2010 | Harris et al. |
| 2010/0237132 A1 | 9/2010 | Measamer et al. |
| 2011/0066167 A1 | 3/2011 | Harris et al. |
| 2012/0160891 A1 | 6/2012 | Harris et al. |
| 2012/0165604 A1 | 6/2012 | Stokes et al. |
| 2012/0165842 A1 | 6/2012 | Stokes et al. |
| 2013/0153622 A1 | 6/2013 | Felder et al. |
| 2013/0153623 A1 | 6/2013 | Felder et al. |
| 2013/0153624 A1 | 6/2013 | Felder et al. |
| 2013/0153625 A1 | 6/2013 | Felder et al. |
| 2013/0153626 A1 | 6/2013 | Felder et al. |
| 2013/0153642 A1 | 6/2013 | Felder et al. |
| 2013/0253536 A1 | 9/2013 | Harris et al. |

FOREIGN PATENT DOCUMENTS

| | | |
|---|---|---|
| DE | 29720952 U1 | 1/1998 |
| EP | 0 068 046 A2 | 1/1983 |
| EP | 0 330 135 B1 | 5/1994 |
| EP | 0 641 546 A1 | 3/1995 |
| EP | 0 519 704 B1 | 10/1996 |
| EP | 0 579 495 B1 | 9/1997 |
| EP | 0 634 142 B1 | 3/1998 |
| EP | 0 558 993 B1 | 4/1998 |
| EP | 0 838 197 A2 | 4/1998 |
| EP | 0 864 297 A2 | 9/1998 |
| EP | 0 669 102 B1 | 10/1998 |
| EP | 0 768 839 B1 | 12/1998 |
| EP | 0 688 186 B1 | 4/1999 |
| EP | 0 676 953 B1 | 5/1999 |
| EP | 0 751 745 B1 | 5/1999 |
| EP | 0 598 588 B1 | 7/1999 |
| EP | 0 669 103 B1 | 9/1999 |
| EP | 0 768 837 B1 | 5/2000 |
| EP | 0 676 952 B1 | 7/2000 |
| EP | 1 098 597 A1 | 5/2001 |
| EP | 0 674 875 B1 | 11/2001 |
| EP | 0 643 945 B1 | 3/2002 |
| EP | 0 835 642 B1 | 8/2002 |
| EP | 0 746 239 B1 | 9/2002 |
| EP | 0 785 751 B1 | 1/2003 |
| EP | 0 748 612 B1 | 2/2003 |
| EP | 1 284 661 A1 | 2/2003 |
| EP | 0 834 281 B1 | 3/2003 |
| EP | 0 782 411 B1 | 8/2003 |
| EP | 1 334 695 A1 | 8/2003 |
| EP | 0 847 727 B1 | 2/2004 |
| EP | 1 202 672 B1 | 3/2004 |
| EP | 1 346 699 B1 | 1/2005 |
| EP | 1 530 441 A2 | 5/2005 |
| EP | 1 281 355 B1 | 9/2005 |
| EP | 1 067 872 B1 | 3/2006 |
| EP | 1 631 201 A1 | 3/2006 |
| EP | 1 648 279 A2 | 4/2006 |
| EP | 1 656 891 A1 | 5/2006 |
| EP | 1 628 581 B1 | 3/2007 |
| EP | 1 584 295 B1 | 2/2008 |
| EP | 1 386 585 B1 | 4/2008 |
| EP | 1 908 423 A2 | 4/2008 |
| EP | 1 632 186 B1 | 6/2008 |
| EP | 1 658 010 B1 | 6/2008 |
| EP | 1 629 780 B1 | 9/2008 |
| EP | 1 507 481 B1 | 12/2008 |
| EP | 1 392 179 B1 | 9/2009 |
| EP | 0 951 238 B1 | 4/2010 |
| EP | 1 259 155 B1 | 12/2010 |
| EP | 1 447 052 B1 | 2/2012 |
| EP | 1 602 336 B1 | 4/2012 |
| GB | 1 549 666 A | 8/1979 |
| JP | 07-265323 A | 10/1995 |
| JP | 2004-508091 A | 3/2004 |
| JP | 2004-160255 A | 6/2004 |
| JP | 2004-520154 A | 7/2004 |
| JP | 2004-216192 A | 8/2004 |
| JP | 2004-358045 A | 12/2004 |
| JP | 2005-530567 A | 10/2005 |
| JP | 2006-307874 A | 11/2006 |
| JP | 2008-279260 A | 11/2008 |
| JP | 2008-543371 A | 12/2008 |
| JP | 2009-000502 A | 1/2009 |
| JP | 2009-236245 A | 10/2009 |
| WO | 92/04870 A1 | 4/1992 |
| WO | 94/14416 A1 | 7/1994 |
| WO | 94/14417 A1 | 7/1994 |
| WO | 94/15535 A1 | 7/1994 |
| WO | 95/29637 A1 | 11/1995 |
| WO | 96/14797 A1 | 5/1996 |
| WO | 96/14798 A1 | 5/1996 |
| WO | 96/41574 A2 | 12/1996 |
| WO | 97/24988 A1 | 7/1997 |
| WO | 99/02107 A1 | 1/1999 |
| WO | 00/57796 A1 | 10/2000 |
| WO | 00/061012 A1 | 10/2000 |
| WO | 00/69345 A1 | 11/2000 |
| WO | 00/74565 A1 | 12/2000 |
| WO | 01/10312 A1 | 2/2001 |
| WO | 01/66001 A2 | 9/2001 |
| WO | 01/66018 A1 | 9/2001 |
| WO | 01/76489 A1 | 10/2001 |
| WO | 01/89393 A1 | 11/2001 |
| WO | 02/30293 A1 | 4/2002 |
| WO | 02/030293 A1 | 4/2002 |
| WO | 02/087481 A1 | 11/2002 |
| WO | 02/094108 A2 | 11/2002 |
| WO | 02/98302 A1 | 12/2002 |
| WO | 03/007796 A2 | 1/2003 |
| WO | 03/065904 A1 | 8/2003 |
| WO | 03/077772 A1 | 9/2003 |
| WO | 03/096910 A1 | 11/2003 |
| WO | 2004/004577 A2 | 1/2004 |
| WO | 2004/014237 A1 | 2/2004 |
| WO | 2004/019788 A2 | 3/2004 |
| WO | 2004/024006 A1 | 3/2004 |
| WO | 2004/041119 A2 | 5/2004 |
| WO | 2004/045378 A2 | 6/2004 |
| WO | 2004/049958 A1 | 6/2004 |
| WO | 2004/086984 A1 | 10/2004 |
| WO | 2004/103189 A1 | 12/2004 |
| WO | 2004/103430 A1 | 12/2004 |
| WO | 2004/105620 A1 | 12/2004 |
| WO | 2005/011463 A2 | 2/2005 |
| WO | 2005/011519 A2 | 2/2005 |
| WO | 2005/020802 A2 | 3/2005 |
| WO | 2005/027754 A1 | 3/2005 |
| WO | 2005/034729 A2 | 4/2005 |
| WO | 2005/039428 A2 | 5/2005 |

(56) References Cited

FOREIGN PATENT DOCUMENTS

| WO | 2005/058239 A2 | 6/2005 |
|---|---|---|
| WO | 2005/060882 A1 | 7/2005 |
| WO | 2005/086945 A2 | 9/2005 |
| WO | 2005/094933 A2 | 10/2005 |
| WO | 2005/096958 A2 | 10/2005 |
| WO | 2005/096994 A1 | 10/2005 |
| WO | 2005/099591 A2 | 10/2005 |
| WO | 2005/107650 A2 | 11/2005 |
| WO | 2005/110241 A1 | 11/2005 |
| WO | 2005/110244 A1 | 11/2005 |
| WO | 2005/110280 A2 | 11/2005 |
| WO | 2005/112784 A2 | 12/2005 |
| WO | 2005/112785 A2 | 12/2005 |
| WO | 2005/112786 A2 | 12/2005 |
| WO | 2005/112797 A1 | 12/2005 |
| WO | 2005/115256 A2 | 12/2005 |
| WO | 2005/122914 A2 | 12/2005 |
| WO | 2005/122954 A1 | 12/2005 |
| WO | 2006/007576 A2 | 1/2006 |
| WO | 2006/019868 A2 | 2/2006 |
| WO | 2006/023165 A2 | 3/2006 |
| WO | 2006/034484 A2 | 3/2006 |
| WO | 2006/037639 A1 | 4/2006 |
| WO | 2006/039199 A2 | 4/2006 |
| WO | 2006/039223 A2 | 4/2006 |
| WO | 2006/039296 A2 | 4/2006 |
| WO | 2006/044837 A2 | 4/2006 |
| WO | 2006/055388 A2 | 5/2006 |
| WO | 2006/055804 A2 | 5/2006 |
| WO | 2006/134106 A1 | 12/2006 |
| WO | 2007/019268 A2 | 2/2007 |
| WO | 2007/095096 A2 | 8/2007 |
| WO | 2008/043044 A2 | 4/2008 |
| WO | 2008/087635 A2 | 7/2008 |
| WO | 2008/088850 A2 | 7/2008 |
| WO | 2008/109876 A1 | 9/2008 |
| WO | 2008/112942 A2 | 9/2008 |
| WO | 2008/118928 A2 | 10/2008 |
| WO | 2009/137517 A1 | 11/2009 |
| WO | 2010/085725 A1 | 7/2010 |
| WO | 2012/103286 A1 | 8/2012 |
| WO | 2012/103291 A1 | 8/2012 |

OTHER PUBLICATIONS

U.S. Appl. No. 12/975,691, entitled, "Endoluminal Fold Creation," filed Dec. 22, 2010.
U.S. Appl. No. 13/164,963, entitled, "A Method of Using a Surgical Stapler to Secure a Tissue Fold," filed Jun. 21, 2011.
[NoAuthorListed] GenBank Accession No. NP_000720. Cholecystokinin preproprotein [*Homo sapiens*]. Dec. 20, 2010 (3 Pages.).
[NoAuthorListed] GenBank Accession No. NP_004151. Peptide YY preproprotein [*Homo sapiens*]. Oct. 31, 2010 (3 Pages).
[NoAuthorListed] GenBank Accession No. P01275. RecName: Full=Glucagon; Contains: RecName: Full=Glicentin; contains: RecName: Full=Glicentin-related polypeptide; Short=GRPP; Contains: RecName: Full=Oxyntomodulin; Short=OXM; Short=OXY; Contains: RecName: Full=Glucagon; Contains: RecName: Full=Glucagon-like peptide 1; Short=GLP-1; Contains: RecName: Full=Glucagon-like peptide 1(7-37); Short=GLP-1(7-37); Contains: RecName: Full=Glucagon-like peptide 1(7-36); Short=GLP-1(7-36); Contains: RecName: Full=Glucagon-like peptide 2; Short=GLP-2; Flags: Precursor. Nov. 30, 2010 (7 Pages).
Archer-Lahlou et al., Molecular mechanism underlying partial and full agonism mediated by the human a cholecystokinin-1 receptor. J Biol Chem. Mar. 18, 2005;280(11):10664-74. Epub Jan. 4, 2005.
Bojanowska, E., Physiology and pathophysiology of glucagon-like peptide-1 (GLP-1): the role of GLP-1 in the pathogenesis of diabetes mellitus, obesity, and stress. Med Sci Monit. Aug. 2005;11(8):RA271-8. Epub Jul. 25, 2005.

Brethauer, et al 'Laparoscopic gastric plication for the treatment of severe obesity' Surg Obest Relat Dis 2011; 7:15-22.
Brethauer, SA, Harris Initial results of vertical gastric plication of severe obesity. Society of American Gastrointestinal and Endoscopic Surgeons. Phoenix Arizona Apr. 22-25, 2009.
Crainich, L. 'Forming a 90 deg. Bend' Metal Forming Magazine (1991) vol. 25, No. 8 pp. 59-60.
Crainich, L. 'Fractures in Metal Stampings' Metal Forming Magazine (1996) pp. 84-85.
European Search Report dated Oct. 1, 2012, Application No. 12172808.3.
European Search Report dated Oct. 1, 2012, Application No. 12172811.7.
European Search Report dated Oct. 1, 2012, Application No. 12172816.6.
Fusco PEB, Poggelli RS, Younes RN, Fontes B, Birolini D. Comparison of Anterior Gastric Wall and Greater Gastric Curvature Invaginations for Weight Loss in Rats. Obes Surg 2007; 17: 1340-5.
Fusco PEB, Poggelli RS, Younes RN, Fontes B, Birolini D. Evaluation of Gastric Greater Curvature Invagination for Weight Loss in Rats. Obes Surg 2006; 16:171-7.
Huang et al 'Novel bariatric technology: laparoscopic adjustable gastric banded plication: technique and preliminary results' Surg Obes Relat Dis, 2012, v8, pp. 41-47 epub Mar. 2011.
International Search Report dated Jun. 1, 2010 (PCT/US2010/021929).
International Preliminary Report dated Jul. 26, 2011, International Application No. PCT/US2010/021929.
International Search Report dated Aug. 13, 2010 (PCT/US2010/021953).
International Preliminary Report dated Jul. 26, 2011, International Application No. PCT/US2010/021953.
International Search Report dated Jun. 4, 2010 (PCT/US2010/021955).
International Preliminary Report dated Jul. 26, 2011, International Application No. PCT/US2010/021955.
International Search Report dated Jan. 25, 2011 (PCT/US2010/053736).
International Preliminary Report dated May 1, 2012, International Application No. PCT/US2010/053736.
International Search Report dated Apr. 7, 2011 (PCT/US2011/020472).
International Preliminary Report dated Jul. 24, 2012, International Application No. PCT/US2011/020472.
International Search Report dated Apr. 5, 2011 (PCT/US2011/020476).
International Preliminary Report dated Jul. 24, 2012, International Application No. PCT/US2011/020476.
International Search Report dated Apr. 3, 2012 for Application No. PCT/US2011/065026 (6 pages).
International Preliminary Report dated Jun. 25, 2013, International Application No. PCT/US2011/065026.
International Search Report dated Apr. 3, 2012 (PCT/US2011/065027).
International Preliminary Report dated Jun. 25, 2013, International Application No. PCT/US2011/065027.
International Search Report dated Apr. 10, 2012 (PCT/US2012/022651).
International Preliminary Report dated Jul. 30, 2013, International Application No. PCT/US2012/022651.
International Search Report dated Apr. 10, 2012 (PCT/US20121022656).
International Preliminary Report dated Jul. 30, 2013, International Application No. PCT/US2012/022656.
International Search Report for Application No. PCT/U52012/068133 dated May 27, 2013 (20 pages).
International Search Report dated Jun. 17, 2014 International Application No. PCT/US2012/068133.
Kobelt et al., Anti-ghrelin Spiegelmer NOX-B11 inhibits neurostimulatory and orexigenic effects of peripheral ghrelin in rats. Gut. Jun. 2006;55(6):788-92. Epub Jun. 30, 2005.

(56) References Cited

OTHER PUBLICATIONS le Roux, et al., Attenuated peptide YY release in obese subjects is associated with reduced satiety. Endocrinology. Jan. 2006;147(1):3-8. Epub Sep. 15, 2005.
Menchaca et al 'Gastric plication: preclinical study of durability of serosa-to-serosa apposition' Surg Obes Relat Dis 2011; 7: 8-14.
Miskowiak et al., Meal stimulated levels of pancreatic polypeptide (PP) and vasoactive intestinal polypeptide (VIP) in gastroplasty for morbid obesity. Regul Pept. Nov. 7, 1985;12(3):231-6.
Qin et al., The role of apolipoprotein AIV on the control of food intake. Curr Drug Targets. Mar. 2005;6(2):145-51.
Ramos, AC 2009 'Tubular sleeve gastroplasty (TSG) as a new approach to bariatric treatment' 14th World Congress of the International Federation for the Surgery of Obesity—Paris, France—Aug. 26-29, 2009.
Sales Puccini, CE. "Surset gastrica de Sales: una alternativa para cirugia bariatrica restrictiva." Rev Colom Cir 2008; 23(3): 131-5 (w/English abstract).
Stanley et al., Gastrointestinal satiety signals III. Glucagon-like peptide 1, oxyntomodulin, peptide YY, and pancreatic polypeptide. Am J Physiol Gastrointest Liver Physiol. May 2004;286(5):G693-7.
Talebpour, M, Amoli BS Laparoscopic Total Gastric Vertical Plication in Morbid Obesity. Journal of Laparoendosc Adv Surg tech A 2007; 17:793-8.
U.S. Appl. No. 11/779,314, filed Jul. 18, 2007, first named inventor Mark S. Zeiner.
U.S. Appl. No. 11/779,322, filed Jul. 18, 2007, first named inventor Mark S. Zeiner.
U.S. Appl. No. 12/113,829, filed May 1, 2008, first named inventor Mark S. Zeiner.
U.S. Appl. No. 12/179,600, filed Jul. 25, 2008, first named inventor Mark S. Zeiner.
U.S. Appl. No. 12/608,860, filed Oct. 29, 2009, first named inventor Jason L. Harris, U.S. Publication No. US-2010-0191282-A1.
U.S. Appl. No. 12/690,311, filed Jan. 20, 2010, first named inventor Lawrence Crainich, U.S. Publication No. US-2010-0187283-A1.
U.S. Appl. No. 12/975,691 entitled 'Endoluminal Fold Creation' filed Dec. 22, 2010.
U.S. Appl. No. 12/975,685, filed Dec. 22, 2010, entitled 'Endoluminal Fold Creation' filed Dec. 22, 2010.
U.S. Appl. No. 12/359,351, filed Jan. 26, 2009, U.S. Publication No. US-2010-0191262-A1.
U.S. Appl. No. 12/359,354, filed Jan. 26, 2009, U.S. Publication No. 12/359354.
U.S. Appl. No. 12/359,357, filed Jan. 26, 2009, U.S. Publication No. US-2010-0191258-A1.
U.S. Appl. No. 12/609,336, filed Oct. 30, 2009, US Publication No. US-2010-0191255-A1.
U.S. Appl. No. 12/690,285, filed Jan. 20, 2010, U.S. Publication No. US-2010-0187284-A1.
U.S. Appl. No. 13/015,966, filed Jan. 28, 2011, U.S. Publication No. US-2012-0125971-A1.
U.S. Appl. No. 13/015,977, filed Jan. 28, 2011, U.S. Publication No. US-2012-0111919-A1.
U.S. Appl. No. 13/164,949, filed Jun. 21, 2011, U.S. Publication No. US-2012-0193394-A1.
U.S. Appl. No. 13/164,954, filed Jun. 21, 2011, U.S. Publication No. US-2012-0193399-A1.
U.S. Appl. No. 13/164,960, filed Jun. 21, 2011, U.S. Publication No. US-2012-0160890-A1.
U.S. Appl. No. 13/164,963, filed Jun. 21, 2011, U.S. Publication No. US-2012-0160891-A1.
U.S. Appl. No. 13/326,625, filed Dec. 15, 2011 to Felder et al.
U.S. Appl. No. 13/362,172, filed Jan. 31, 2012, U.S. Publication No. US-2012-0330329-A1.
U.S. Appl. No. 13/371,678, filed Feb. 13, 2012, U.S. Publication No. US-2013-0193183-A1.
U.S. Appl. No. 13/371,684, filed Feb. 13, 2012, U.S. Publication No. US-2013-0193184-A1.
U.S. Appl. No. 13/911,337, filed Jun. 6, 2013, U.S. Publication No. US-2014-0151435-A1.

* cited by examiner

METHODS AND DEVICES FOR CREATING TISSUE PLICATIONS

CROSS-REFERENCE TO RELATED APPLICATIONS

This application is a continuation of U.S. application Ser. No. 13/425,900, filed on Mar. 21, 2012, now issued as U.S. Pat. No. 8,992,547 and entitled "METHODS AND DEVICES FOR CREATING TISSUE PLICATIONS," which is hereby incorporated by reference in its entirety.

FIELD

This invention relates generally to devices and methods for performing surgical procedures, and more particularly to endoscopic devices and methods for forming endoluminal plications to reduce the volume of the gastric cavity.

BACKGROUND

Metabolic disease is a serious medical condition that affects more than 30% of the U.S. population and can contribute significantly to morbidity and mortality. Complications associated with metabolic disease include obesity, hypertension, diabetes, coronary artery disease, stroke, congestive heart failure, multiple orthopedic problems, pulmonary insufficiency, sleep apnea, infertility, and markedly decreased life expectancy. Additionally, the complications or co-morbidities associated with metabolic disease, such as obesity, often affect an individual's quality of life. Accordingly, the monetary, physical, and psychological costs associated with metabolic disease can be substantial. For example, it is estimated that costs related to obesity alone exceed more than 100 billion dollars annually.

A variety of bariatric surgical procedures have been developed to treat complications of metabolic disease, such as obesity. The most common of these is the Roux-en-Y gastric bypass (RYGB). In a RYGB procedure, a small stomach pouch is separated from the remainder of the gastric cavity and attached to a resectioned portion of the small intestine. However, because this complex procedure requires a great deal of operative time, as well as extended and often painful post-operative recovery, the RYGB procedure is generally only utilized to treat people with morbid obesity.

In view of the highly invasive nature of the RYGB procedure, other less invasive bariatric procedures have been developed such as the Fobi pouch, bilio-pancreatic diversion, gastroplasty ("stomach stapling"), vertical sleeve gastrectomy, and gastric banding. In addition, implantable devices are known which limit the passage of food through the stomach. Gastric banding procedures, for example, involve the placement of a small band around the stomach near the junction of the stomach and the esophagus to restrict the passage from one part of the digestive tract to another, thereby affecting a patient's feeling of satiety.

While the above-described bariatric procedures are commonly used for the treatment of morbid obesity (i.e., greater than 100 pounds over one's ideal body weight), the risks of these procedures often outweigh the potential benefits for the growing segment of the population that is considered overweight. The additional weight carried around by these persons can still result in significant health complications, but does not justify more invasive treatment options. However, because conservative treatment with diet and exercise alone may be ineffective for reducing excess body weight, there is a need for treatment options that are less invasive and lower cost than the procedures discussed above.

It is known to create cavity wall plications through both laparoscopic and endoscopic procedures. Laparoscopic plication techniques can be complicated and complex, however, as one or more surgical entry ports must be employed to gain access to the surgical site. Furthermore, laparoscopically approaching the stomach often requires separating the surrounding omentum prior to plication formation. In endoscopic procedures, plication depth has traditionally suffered due to the size restrictions of the endoscopic lumen. For example, the rigid length and diameter of a surgical device are limited based on what sizes can be reliably and safely passed trans-orally into the stomach. Furthermore, access and visibility within the gastric and peritoneal cavities is progressively limited in an endoscopic procedure as the extent of the reduction increases because the volume of the gastric cavity is reduced.

In addition, prior art devices for forming endoluminal plications often utilize opposing jaws and a grasper element to draw tissue between the jaws. The prior art devices approach the cavity wall such that a longitudinal axis of the device is perpendicular to the cavity wall. The grasper element can then be advanced along a parallel axis, and used to draw tissue into the jaws to create the fold. One exemplary prior art device is described in U.S. Patent Publication No. 2005/0251166 to Vaughan et al., the contents of which are hereby incorporated by reference in their entirety.

FIG. 1A illustrates the device disclosed by Vaughan et al., which includes a tubular body 12 connected to a lower jaw 20. The lower jaw is in turn connected to an upper jaw 22, and the upper jaw is connected to a launch tube 44. By moving the launch tube proximally and distally, the jaws can be moved between the positions shown in FIGS. 1A and 1B.

In use, the device disclosed by Vaughan et al. is extended from a transport device, such as an endoscope, and positioned such that a longitudinal axis of the device is perpendicular to a tissue wall. A tissue grasping element 102 is utilized to grab the tissue wall and pull it into the open jaws, as shown in FIG. 2. The jaws are then moved to a closed position and a fastener is delivered through the launch tube 44 to secure the plication.

However, the geometry of the device limits the size of the plication that can be formed to approximately the length of the jaws, as the grasper can only draw the cavity wall tissue to the center of the jaws and no farther. This maximum fold depth D is shown in the side view of the device of Vaughan et al. shown in FIG. 3.

Accordingly, it is desirable to have methods and devices for forming tissue folds, such as serosa-to-serosa tissue folds within the gastric lumen, that overcome the aforementioned problems.

SUMMARY

The present invention generally provides devices and methods for forming and securing plications of tissue. More particularly, the devices and methods of the present invention can be used to create and secure plications of gastric tissue on the anterior and posterior walls of a patient's gastric cavity to reduce the volume of the cavity. Particular features of the devices and methods described herein provide advantages over prior art devices including, for example, the ability to create plications having a depth greater than a length of the surgical instrument used to secure the plication.

In one aspect, a tissue manipulation device is provided that includes a first jaw member pivotally coupled to a distal end of an elongate shaft at a proximal end thereof, the first jaw member having an articulating portion located distal to the proximal end of the first jaw member. The device further includes a second jaw member pivotally coupled to the first jaw member at a location distal to the articulating portion, the first and second jaw members being configured to open in a first plane. The device also includes a fastener delivery member attached to the second jaw member and having an inner lumen extending therethrough. The articulating portion of the first jaw member can be configured to move the first and second jaw members between a straight configuration in which a longitudinal axis of the elongate shaft is contained within the first plane and an articulated configuration in which the longitudinal axis of the elongate shaft is transverse to the first plane.

By articulating the first and second jaw members into a position transverse to the longitudinal axis of the elongate shaft, the first and second jaw members can avoid the limitations discussed above related to the depth of folds that can be created using the jaws. This can be accomplished, for example, by pulling tissue transversely through the jaws rather than into the open jaws toward their center pivot. For example, in some embodiments, the longitudinal axis of the elongate shaft can be perpendicular to the first plane in the articulated configuration. As a result, if the elongate shaft approaches a tissue wall along a perpendicular axis, the first and second jaws can be articulated such that they are parallel to the tissue wall. Tissue can then be drawn through the jaws from one side to another, allowing the creation of a tissue fold of any depth.

The articulating portion of the tissue manipulation device can have a variety of forms. For example, in some embodiments, the articulating portion can include a hinge. The hinge can be formed in the first jaw member and positioned between the attachment of the first jaw member to the elongate shaft and the connection to the second jaw member. In other embodiments, the articulating portion can include a plurality of jointed segments. Each segment can be configured to provide a certain range of motion, such that the plurality together can provide a greater range of motion. The number of segments can be selected according to the desired total amount of articulation (e.g., 90 degrees, greater than 90 degrees, etc.), the degree of motion provided by each individual segment, the desired length of the device, etc. In still other embodiments, the articulating portion can include a ball-and-socket joint. Alternatively, the articulating portion can comprise a plurality of ball-and-socket joints similar to the plurality of jointed segments described above.

In some embodiments, the device can further include an articulation actuating member configured to control the articulating portion. The articulation actuating member can have a number of different forms. For example, in some embodiments, the articulation actuating member can include one or more connecting members extending proximally from a location distal to the articulating portion. The connecting members can have a variety of forms, including cables, wires, ribbons, bands, etc. In such an embodiment, the one or more connecting members can be pulled to effect movement of the first and second jaws via movement of the articulating portion. A number of other embodiments of the articulation actuating member are possible as well. These include, for example, shape memory materials, electrically driven actuators, etc. In certain embodiments, the one or more cables or other connecting members of an articulation actuating member can be contained in a lumen of a sheath covering the articulating portion. A sheath or other protective covering can be employed to cover other embodiments of an articulation actuating member (e.g., springs, linkages, etc.) to prevent protrusions from interfering with use of the device inside a patient's body.

The first and second jaw members of the tissue manipulation device can be operated by movement of the fastener delivery member whether in the straight configuration or articulated configuration. For example, in some embodiments, the second jaw member can have a channel formed therein and the fastener delivery member can be configured to urge the first and second jaw members between a low-profile delivery configuration in which a distal portion of the fastener delivery member is positioned substantially within the channel and an open configuration in which the distal portion of the fastener delivery member is positioned substantially outside of the channel. Movement of the fastener delivery member in the proximal direction can, in some embodiments, urge the first and second jaw members into an open position. Conversely, movement of the fastener delivery member in the distal direction can urge the first and second jaw members into a close configuration effective to grasp tissue disposed therebetween.

The fastener delivery member itself can have a variety of configurations. In some embodiments, the distal end of the fastener delivery member can be pivotally coupled to the second jaw member. In other embodiments, the fastener delivery member can include a distally located flexible portion. In certain embodiments, the fastener delivery member can also include a rigid portion proximal to the flexible portion. The combination of the rigid and flexible portions can be utilized to impart urging force to the first and second jaw members in a variety of positions in either the straight or articulated configurations.

In some embodiments, the fastener delivery member can include a fastener deployment assembly within the inner lumen of the fastener delivery member. The fastener deployment assembly can be configured to introduce a fastener through tissue disposed between the first and second jaw members to secure a tissue plication. This can be accomplished in a variety of manners. For example, in some embodiments, the fastener deployment assembly can include a needle having a tip moveable out of the fastener delivery member and through openings formed in the first and second jaw members. The needle can include an inner lumen in which one or more fasteners are disposed. A variety of different fasteners can be employed and, in some embodiments, each fastener can include two anchors joined by a suture or other connecting element. A first anchor can be ejected from the fastener delivery member on a first side of tissue disposed between the first and second jaw members, and a second anchor can be ejected from the fastener delivery member on a second side of the tissue. The connecting suture can be utilized to maintain the two tissue interfacing elements in close apposition to secure the tissue fold. Alternatively, both anchors can be ejected on a same side of tissue at two locations, with the connecting suture passing through the tissue and extending between the two anchors.

In another aspect, a tissue acquisition and fixation system is provided that includes an elongate shaft having proximal and distal ends, and an end effector having first and second jaws configured to pivot in a first plane. The end effector can be coupled to the distal end of the elongate shaft and configured to pivot relative to the elongate shaft in a second plane that is transverse to the first plane. The system can further include a flexible fastener delivery member extending from the elongate shaft and coupled to the second jaw, as well as a tissue grasper capable of moving independently from the end effector and configured to draw tissue through the first and second jaws.

In some embodiments, the end effector can be configured to move between an insertion configuration in which a longitudinal axis of the elongate shaft is contained within the first plane and a grasping configuration in which the longitudinal axis of the elongate shaft is transverse to the first plane. This movement can be similar to the device described above. In certain embodiments, the longitudinal axis of the elongate shaft can be perpendicular to the first plane in the grasping configuration.

In still another aspect, a method of acquiring and fixating tissue is provided that includes inserting into a body lumen a tissue grasper, an elongate shaft, and an end effector having first and second jaws that are pivotally coupled to a distal end of the elongate shaft. The method further includes pivoting the end effector with respect to the elongate shaft in a first plane, and pivoting the first and second jaws in a second plane that is transverse to the first plane. The method also includes positioning the tissue grasper to engage tissue, drawing tissue through the first and second jaws by moving the tissue grasper transversely with respect to the first and second jaws, and delivering a fastener through the tissue disposed between the first and second jaws from a fastener delivery member coupled to the second jaw.

In some embodiments, inserting the end effector and elongate shaft into a body lumen can include positioning the elongate shaft perpendicular to an inner surface of the body lumen. Further, pivoting the end effector in the first plane can include positioning the end effector such that a longitudinal axis of the end effector is parallel to the inner surface of the body lumen. In this position, tissue can be drawn through the first and second jaws in a transverse direction (i.e., a direction transverse to a longitudinal axis of the first and second jaws) by moving the tissue grasper transversely with respect to the first and second jaws. Furthermore, in some embodiments, moving the tissue grasper transversely with respect to the first and second jaws can include moving the tissue grasper perpendicular to a longitudinal axis of the first and second jaws. In this configuration, tissue can be drawn through the jaws to any depth, as the pivotal connection between the first and second jaws does not impede the progress of the tissue.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Figure 1A:
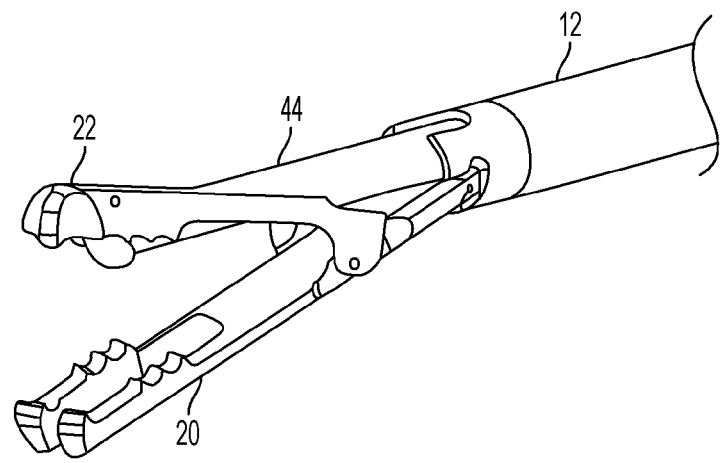
FIG. 1A is an illustration of a prior art tissue manipulation device in an open jaw configuration.
Figure 1B:
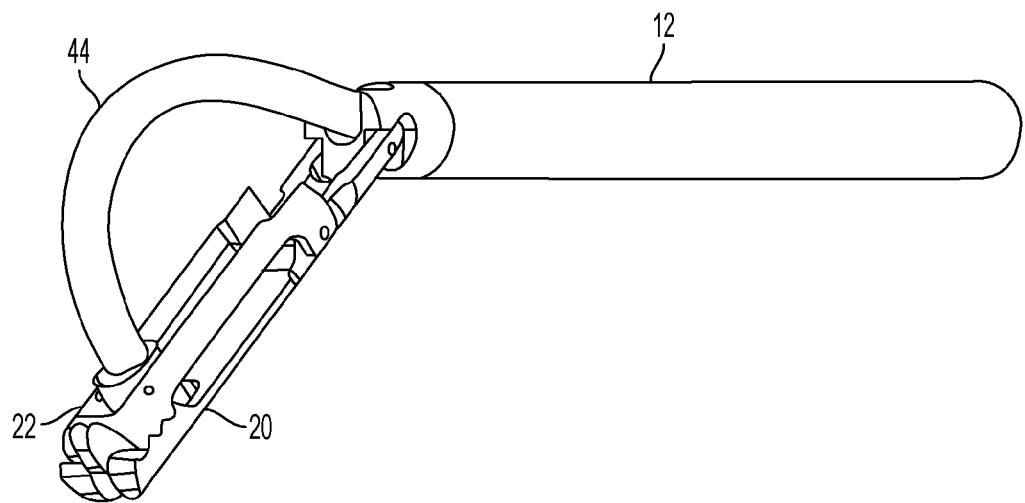
FIG. 1B is an illustration of the prior art tissue manipulation device of FIG. 1A in a closed jaw configuration.

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. The terms "about" and "approximately" used for any numerical values or ranges indicate a suitable dimensional tolerance that allows the composition, part, or collection of elements to function for its intended purpose as described herein. These terms generally indicate a ±10% variation about a central value. Components described herein as being coupled may be directly coupled, or they may be indirectly coupled via one or more intermediate components. The recitation of any ranges of values herein is merely intended to serve as a shorthand method of referring individually to each separate value falling within the range, unless otherwise indicated herein, and each separate value is incorporated into the specification as if it were individually recited. All methods described herein can be performed in any suitable order unless otherwise indicated herein or otherwise clearly contradicted by context. The use of any and all examples, or exemplary language (e.g., "such as"), provided herein is intended merely to better illuminate the invention and does not impose a limitation on the scope of the invention unless otherwise claimed. No language in the specification should be construed as indicating any non-claimed element as essential to the practice of the invention.

The present invention generally provides devices and methods for apposing, forming, and securing tissue plications. These generally involve the creation of tissue plications for the reduction of cavity capacity, but may include the closure or repair of intentional (gastrotomy, colotomy, or enterotomy closure from Natural Orifice Translumenal Endoscopic Surgery (NOTES™), etc.) or unintentional (fistula, gastrointestinal leaks, etc.) tissue defects as well as the creation valves or restrictions to alter (e.g., enhance or impede) the flow of substances (e.g., Nissen fundoplication). In general, devices are provided having a set of pivoting jaws that can be articulated such that the jaws can be positioned parallel to a tissue wall and a tissue grasper can be used to draw tissue through the open jaws transversely. One or more of the jaws can be coupled to the distal end of an elongate shaft or other surgical instrument that can be configured, for example, to be inserted into a patient's stomach through the esophagus. The surgical instrument itself can also include an articulating portion to allow the jaws to be positioned in a range of locations on, for example, both the anterior and posterior inner walls of the stomach. In use, the surgical instrument can approach a tissue wall along a perpendicular axis thereof and the jaws can be articulated to a position parallel to the tissue wall. A tissue grasper can then be used to engage the tissue wall and draw tissue through the open jaws by moving transversely across the jaws, thereby forming a tissue plication, or fold, disposed between the jaws. The jaws can then be closed and a fastener applied through a tube connected to the jaws to secure the plication.

By forming and fastening one or more of these plications, the volume or capacity of a cavity, such as the gastric cavity, can be reduced without the need for more invasive surgical procedures. The devices and methods of the present invention can be used to treat a wide variety of complications that develop as a result of metabolic disease. One common example of such a complication is obesity. However, non-obese individuals suffering from other metabolic disease complications, such as patients with low-Body Mass Index (BMI) type 2 diabetes, can also be treated using the teachings of the present invention.

As noted above, the devices disclosed herein can be at least partially positioned inside a patient's body cavity through an orifice for minimally invasive surgical procedures. Typically, the devices are inserted through a patient's mouth and extended down their esophagus into the stomach. However, one skilled in the art will appreciate that any of the surgical device components disclosed herein can also be adapted for use in other surgical procedures, whether minimally invasive or open.

The various components of the devices disclosed herein can be formed from any of a variety of materials known in the art and suitable for use in surgical devices. For example, the various components can be formed from metal (e.g., stainless steel, titanium, or other biocompatible metals), plastic (e.g., polyetheretherketone (PEEK), polycarbonate, polypropylene, ultem, or other biocompatible polymers), elastomers (e.g., silicone or other biocompatible elastomers) and/or combinations thereof.

Figure 4:
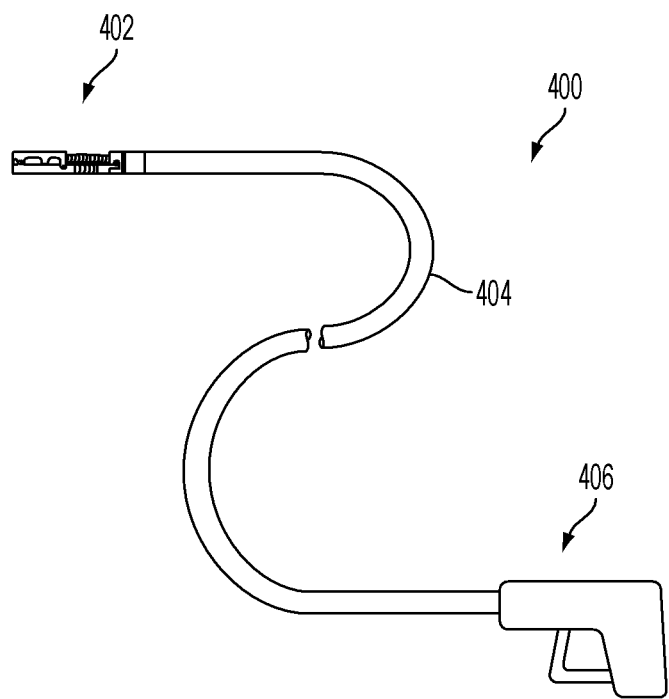
FIG. 4 is an illustration of one embodiment of a surgical instrument featuring a tissue manipulation device of the present invention.

FIG. 4 illustrates one embodiment of a surgical instrument 400 of the present invention. The surgical instrument 400 may be utilized for endoluminally accessing tissue and includes a tissue manipulation device 402 that can create and secure one or more tissue plications. The surgical instrument 400 generally comprises an elongate shaft 404, which may be embodied as a flexible catheter or tubular body, that is configured to be advanced into a body lumen either transorally, percutaneously, laparoscopically, etc. The elongate shaft 404 may be configured to be torqueable through various methods, e.g., utilizing a braided tubular construction, such that when an attached handle 406 is manipulated and/or rotated by a user from outside the patient's body, the longitudinal and/or torqueing force can be transmitted along the elongate shaft 404 such that the distal end of the shaft is advanced, withdrawn, or rotated in a corresponding manner.

Figure 5A:
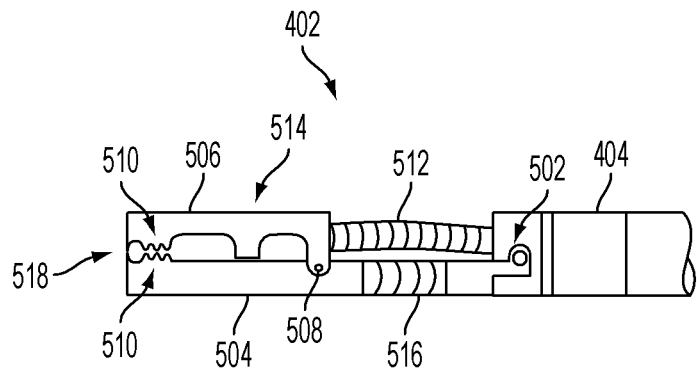
FIG. 5A is a side view of one embodiment of an articulating tissue manipulation device in an insertion configuration.
Figure 5B:
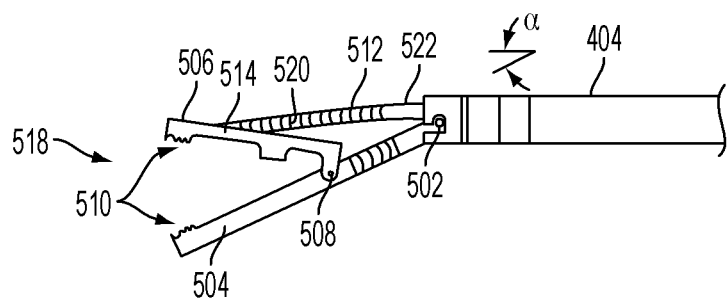
FIG. 5B is a side view of the device of FIG. 5A in an open configuration.
Figure 5C:
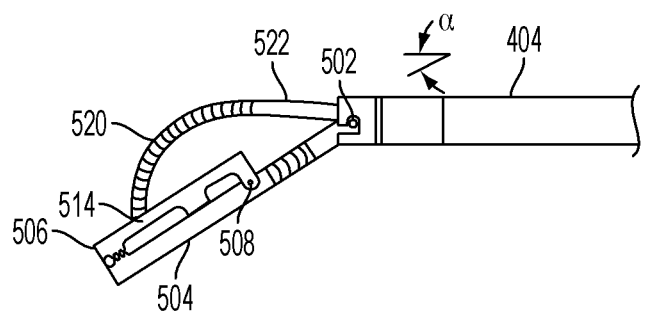
FIG. 5C is a side view of the device of FIG. 5A in a closed configuration.

FIGS. 5A-5C illustrate a side view of one embodiment of a tissue manipulation device 402 that can be disposed as an end effector on the distal end of the elongate shaft 404. The tissue manipulation device is generally used to contact and secure tissue folds. The device 402 can be connected to the distal end of the elongate shaft 404 via a pivotal coupling 502. A first lower jaw member 504 can extend distally from the pivotal coupling 502 and a second upper jaw member 506 can be pivotally coupled to first jaw member via a jaw pivot 508. The position of the jaw pivot 506 can vary along the first jaw 504 depending upon a number of factors including, for example, the desired size of the "bite" or opening for accepting tissue between the first and second jaw members, the amount of closing force applied by the first and second jaw members, etc. One or both of the first and second jaw members 504, 506 can also have a number of protrusions, projections, grasping teeth, textured surfaces, etc., 510 on the surface or surfaces thereof to facilitate the adherence of tissue between the jaw members.

The tissue manipulation device 402 can also include a fastener delivery member 512 that can extend from the handle 406 through the elongate shaft 404 and protrude distally from the end of the elongate shaft. A distal end of the fastener delivery member 512 can be pivotally coupled to the second jaw member 506 at a delivery member pivot 514. A distal portion of the fastener delivery member 512 can be pivoted into position within a channel or groove defined in the second jaw member 506 to facilitate a low-profile configuration of the tissue manipulation device 402, as shown in FIG. 5A. This configuration can be utilized, for example, when introducing the device into a patient's body. The fastener delivery member 512 can also articulate out of the channel in the second jaw member 506 when moved in a proximal or distal direction (as shown in FIGS. 5B and 5C). Furthermore, and as described in more detail below, movement of the fastener delivery member 512 can urge the first and second jaw members 504, 506 into either an open or closed configuration.

For example, the fastener delivery member 512 can be advanced from its proximal end at the handle 406 such that the portion of the fastener delivery member 512 which extends distally from the elongate shaft 404 is forced to rotate at the delivery member pivot 502 and reconfigure itself such that the exposed portion forms a curved or arcuate shape that positions an opening at the distal end of the fastener delivery member to be perpendicular to the second jaw member 506. Such a configuration is shown with respect to the tissue manipulation device illustrated in FIG. 5C. The fastener delivery member 512, or at least the exposed portion thereof, can be fabricated from a highly flexible material or it may be fabricated, e.g., from Nitinol tubing material which is adapted to flex, e.g., via circumferential slots, to permit bending.

The tissue manipulation device 402 can also include an articulation portion 516 configured to allow the first and second jaw members 504, 506 to pivot, rotate, or articulate with respect to the elongate shaft 404. The articulation portion 516 can be positioned anywhere along the tissue manipulation device 402, or between the tissue manipulation device 402 and the elongate shaft 404. In an exemplary embodiment, the articulation portion 516 can be formed along the length of the first jaw member 504 at a position between the pivotal coupling 502 and the jaw pivot 508 (i.e., at a position distal to the proximal end of the first jaw member 504 and proximal to the connection between first jaw member and the second jaw member 506). Positioning the articulating portion 516 in this manner can allow the jaws to be efficiently articulated without requiring additional adjustment of the remainder of the surgical instrument (e.g., the elongate shaft, etc.). In other embodiments, however, the articulating portion 516 can be an intermediate member coupling the first jaw member 504 to the elongate shaft 404. In such an embodiment, the first jaw member 504 can be pivotally coupled to the articulating portion 516, and the articulating portion can in turn be coupled to the distal end of the elongate shaft 404.

Figure 6A:
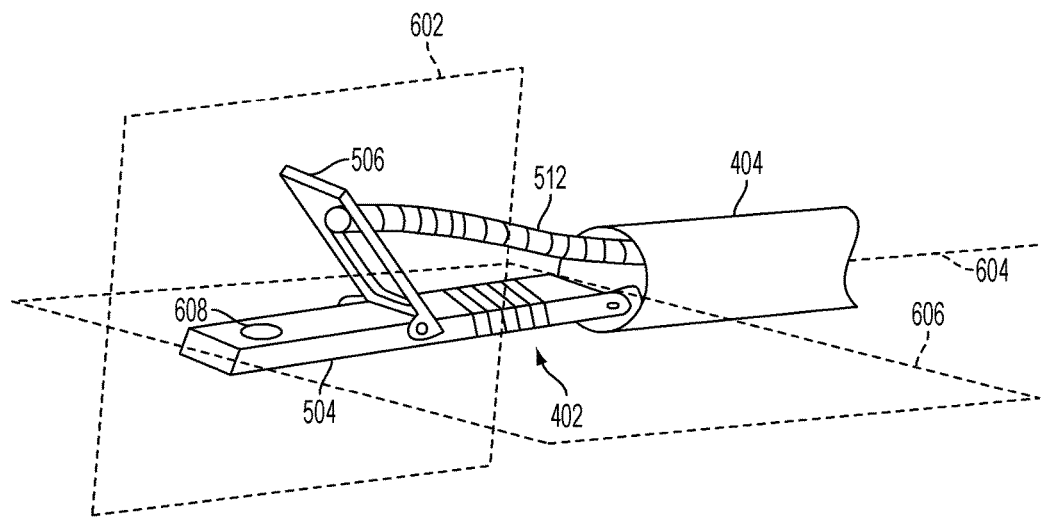
FIG. 6A is a perspective view of the tissue manipulation device of FIG. 5A.
Figure 6B:
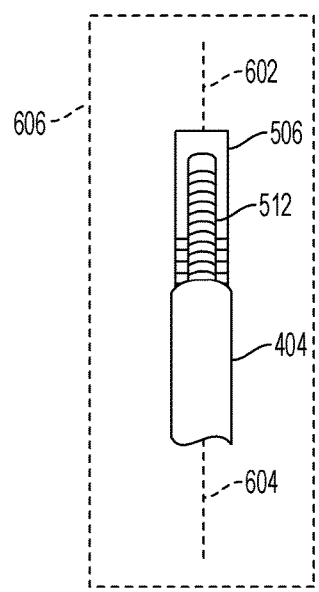
FIG. 6B is a top view of the tissue manipulation device of FIG. 6A.
Figure 6C:
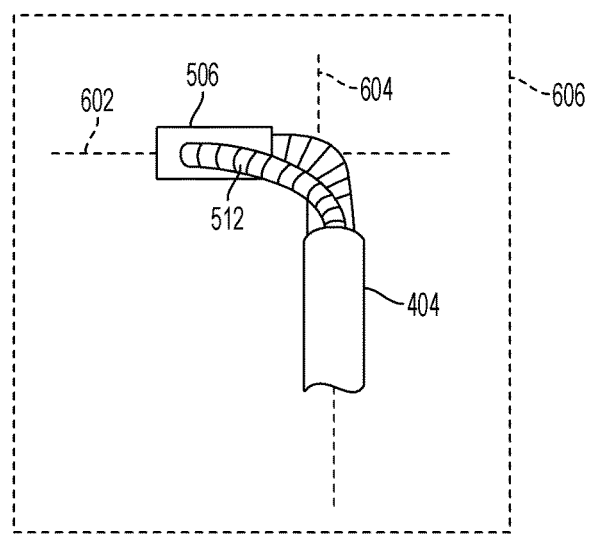
FIG. 6C is a top view of the tissue manipulation device of FIG. 6A in an articulated configuration.

FIGS. 6A-6C illustrate exemplary movement provided by the articulating portion 516. FIG. 6A illustrates the tissue manipulation device 402 in a straight configuration. In this configuration, a first plane 602, defined as the plane in which the first jaw member 504 and the second jaw member 506 move with respect to each other, contains a longitudinal axis 604 of the elongate shaft 404. In other words, the first plane 602 and the longitudinal axis 604 are coplanar. FIG. 6B illustrates a top view of the straight configuration, showing that the first plane 602 contains the longitudinal axis 604 of the elongate shaft 404. This straight configuration, in combination with the low-profile configuration of the first and second jaw members shown in FIG. 5A, can be used to deliver the tissue manipulation device 402 into a patient's body. As mentioned above, the device can be inserted transorally, through an endoscope, an endoscopic device, or directly.

The tissue manipulation device 402 can be advanced to a tissue wall along an axis perpendicular to the tissue wall and, prior to use, can be rotated into a position parallel to the tissue wall by actuating the articulating portion 516. The articulating portion 516 can cause the first and second jaw members 504, 506 to move between the straight configuration shown in FIGS. 6A and 6B to an articulated configuration shown in the top view of FIG. 6C. In the articulated configuration, the first plane 602 (i.e., the plane in which the first and second jaw members open and close) can be transverse to the longitudinal axis 604 of the elongate shaft 404. In other words, the articulation portion 516 can pivot or move the tissue manipulation device 402 with respect to the elongate shaft 404 in a second plane 606 that is transverse to the first plane 602. While the articulating portion 516 can be configured to rotate the first and second jaw members to any degree (e.g., less than 90° from the longitudinal axis 604, or greater than 90° from the longitudinal axis 604), in some embodiments the articulating portion is configured to rotate the first and second jaw members approximately 90° from the longitudinal axis 604 such that the first and second jaw members are substantially parallel to the tissue wall. Such a configuration can allow tissue to be drawn through the first and second jaw members transversely, as is described in more detail below.

Once desirably positioned with respect to a tissue wall, the fastener delivery member 512 can be urged proximally via its proximal end at handle 406. Because of the pivotal coupling 502 and the relative positioning of the jaw pivot 508 along the first jaw member 504 and the delivery member pivot 514 along the second jaw member 506, the proximal movement of the fastener delivery member 512 can effectively articulate the second jaw 506 into an expanded jaw configuration, which is shown in the straight configuration in FIG. 5B. Proximally urging the fastener delivery member 512 can also urge the first jaw member 504 to pivot about the pivotal coupling 502 such that the first jaw member 504 can form an angle relative to a longitudinal axis of the elongate shaft 404. The opening of the second jaw member 506 relative to the first jaw member 504 can create a jaw opening 518 for grasping or receiving tissue. Moreover, the tissue manipulation device 402 can also include a stop located adjacent to the pivotal coupling 502 or within the coupling 502 itself. The effect of moving the fastener delivery member 512 can be identical regardless of whether the tissue manipulation device 402 is in the straight configuration of FIGS. 6A and 6B or the articulated configuration shown in FIG. 6C, though FIGS. 5A-5C show the device in the straight configuration for ease of illustration. These jaw configurations can be identically achieved in the articulated configuration. Furthermore, in use, the actuation of the articulation portion 516 and the fastener delivery member 512 can be performed in any order. For example, the tissue manipulation device 402 can be moved from the straight configuration to the articulated configuration prior to urging the first and second jaw members from the low-profile configuration of FIG. 5A, or the jaw members can be opened prior to articulating the device using the articulation portion 516.

After the fastener delivery member 512 has been urged proximally to create the jaw opening 518, it can be locked into place, thereby locking the jaw configuration as well. Moreover, having the fastener delivery member 512 urge the first and second jaw members 504, 506 in this way eliminates the need for a separate jaw articulation and/or locking mechanism. Once any tissue has been pulled or manipulated between the first and second jaw members 504, 506, as is discussed in more detail below, the fastener delivery member 512 can be advanced distally to urge the first and second jaw members 504, 506 into a closed configuration, as shown in FIG. 5C (jaws are shown in the straight configuration). As the fastener delivery member 512 is advanced distally through the elongate body 404, the first jaw member 504 can be maintained at the same angle relative to the tissue to further facilitate manipulation of the grasped tissue.

The fastener delivery member 512 can include a flexible portion 520 positioned distally of a rigid portion 522. Although the fastener delivery member 512 can be fabricated from a combination of materials having differing flexibilities, it can also be fabricated from a single material, as mentioned above, where the flexible portion 520 can be configured, e.g., by slotting, to allow for bending of the fastener delivery member in a plane to form a single curved or arcuate section while the rigid section 522 can extend at least partially into the elongate shaft 12 to provide column strength to the fastener delivery member while it is urged distally upon the second jaw member 506 and upon any tissue disposed between the first and second jaw members. The flexibility provided by the flexible portion 520 also allows the fastener delivery member 512 to effectively urge the first and second jaw members between the various positions discussed above regardless of whether the tissue manipulation device 402 is in the straight configuration of FIGS. 6A and 6B or the articulated configuration of FIG. 6C.

In order to securely fasten any tissue engaged between the first and second jaw members 504, 506, a fastener deployment assembly 700 (shown in FIG. 7) can be urged through the handle 406 and out through the fastener delivery member 512. The fastener deployment assembly 700 can pass through the tissue disposed between the first and second jaw members and through an opening 608 formed in the first jaw member 504 (shown in FIG. 6A). After the fastener deployment assembly 700 has been passed through the tissue between the first and second jaw members 504, 506, one or more tissue anchors may be deployed for securing the tissue, as described below.

Figure 7:
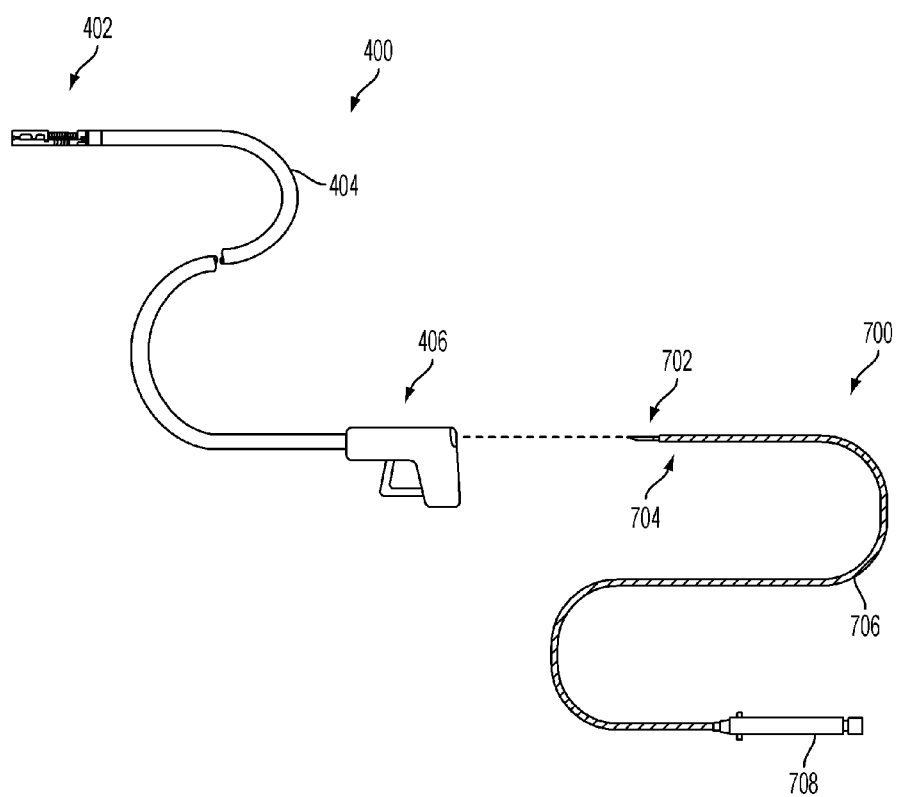
FIG. 7 is an exploded view of the surgical instrument of FIG. 4 and one embodiment of a fastener deployment assembly.

The fastener deployment assembly 700 can be deployed through the surgical instrument 400 by introducing the fastener deployment assembly into the handle 406 and through the elongate shaft 404, as shown in the exploded view of FIG. 7. In particular, a needle assembly 702 can be advanced from the fastener delivery member 512 into or through approximated tissue. After the needle assembly 702 has been advanced through the tissue, an anchor assembly 704 can be deployed or ejected, as described below. The anchor assembly 704 can be positioned within the distal portion of a sheath 706 that extends from a needle control or housing 708. After the anchor assembly 704 has been fully deployed from the sheath 706, the spent fastener deployment assembly 700 can be removed from the surgical instrument 400 and a new or reloaded fastener deployment assembly can be introduced without having to remove the surgical instrument 400 from the patient. The length of the sheath 706 can be such that it can be passed entirely through the length of the elongate shaft 404 to enable the deployment of the needle assembly 702 into and/or through the tissue.

Figure 8:
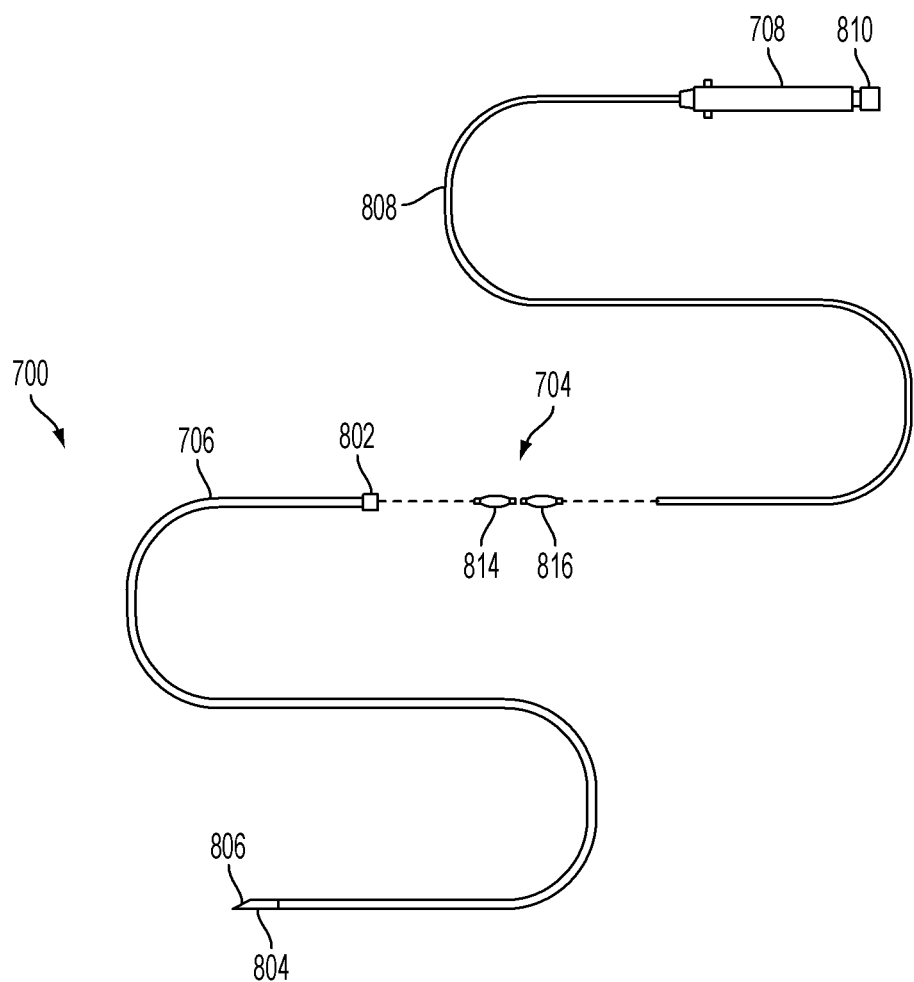
FIG. 8 is an exploded view of the fastener deployment assembly of FIG. 7.

FIG. 8 illustrates a more detailed exploded view of the fastener deployment assembly 700. As shown in the figure, the elongate and flexible sheath or catheter 706 can extend removably from the needle control or housing 708. The sheath 706 and housing 708 can be coupled via an interlock 802 that can be adapted to allow for the securement as well as the rapid release of the sheath 706 from the housing 708 through any number of fastening methods, e.g., threaded connection, press-fit, releasable pin, etc. A needle body 804 can extend from the distal end of the sheath 706 while maintaining communication between an inner lumen of the sheath 706 and an opening 806 formed in a distal end of the needle.

An elongate pusher 808 can comprise a flexible wire that can be translationally disposed within the sheath 706 and movably connected within the housing 708. A proximally-located actuation member 810 may be rotatably or otherwise connected to the housing 708 to selectively actuate the translational movement of the elongate pusher 808 relative to the sheath 706 for deploying the anchors from the needle opening 806. The anchor assembly 704 can be positioned distally of the elongate pusher 808 within the sheath 706 for deployment from the sheath. In use, the elongate pusher 808 can be advanced using the actuation member 810 to push the anchor assembly 704 distally down the sheath 706 and, ultimately, out of the needle opening 806.

The anchor assembly 704 can, in some embodiments, comprise a first distal anchor 814 and a second proximal anchor 816. The anchors 814, 816 can be any of a variety of anchors capable of being delivered through the sheath 706 and expanding or orienting themselves upon ejection so as to exert a force against tissue. The anchors 814, 816 can be connected to each other using a suture or other connecting member such that the first distal anchor 814 can be ejected on a first side of a tissue plication and the second proximal anchor 816 can be ejected on a second side of a tissue plication. Alternatively, in some embodiments both anchors 814, 816 can be ejected on a same side of a tissue plication at two locations, with the suture or connecting member extending through the plication and between the two anchors. The suture or connecting member can be used in conjunction with one or more cinching or locking members to draw the anchors 814, 816 closer together and secure the tissue plication in place.

With respect to the anchor assembly 704 and anchors 814, 816, the types of anchors shown and described are intended to be illustrative and are not limited to the variations shown. Any number of different tissue anchors can be employed with the illustrated device, including, for example, "T-tag" anchors and reconfigurable "basket" anchors that generally comprise a number of configurable struts or legs extending between at least two collars or support members or reconfigurable mesh structures extending between the two collars. An exemplary "T-tag" anchor and one-way sliding knot is disclosed in U.S. Patent Publication No. 2009/0024144 to Zeiner et al., and other exemplary anchors (including "basket" anchors) are disclosed in U.S. Patent Publication No. 2005/0251157 to Saadat et al. and U.S. Pat. No. 7,347,863 to Rothe et al., the contents of which are hereby incorporated by reference in their entirety. Other variations of these or other types of anchors are also contemplated for use in an anchor assembly 704. Moreover, a single type of anchor may be used exclusively in an anchor assembly or a combination of different anchor types may be used in an anchor assembly. Furthermore, the cinching or locking mechanisms disclosed are not intended to be limited to any of the particular variations shown and described but may be utilized in any combination with any of the various types of anchors.

Figure 9:
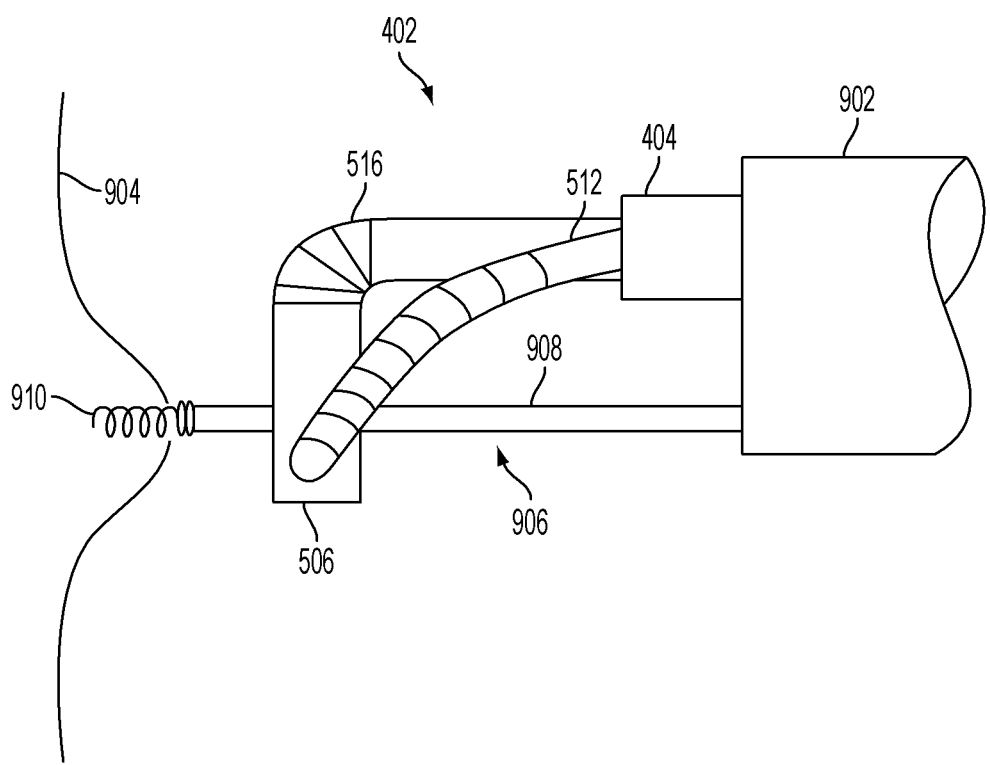
FIG. 9 is a top view of one embodiment of a tissue manipulation device in an articulated configuration.
Figure 10:
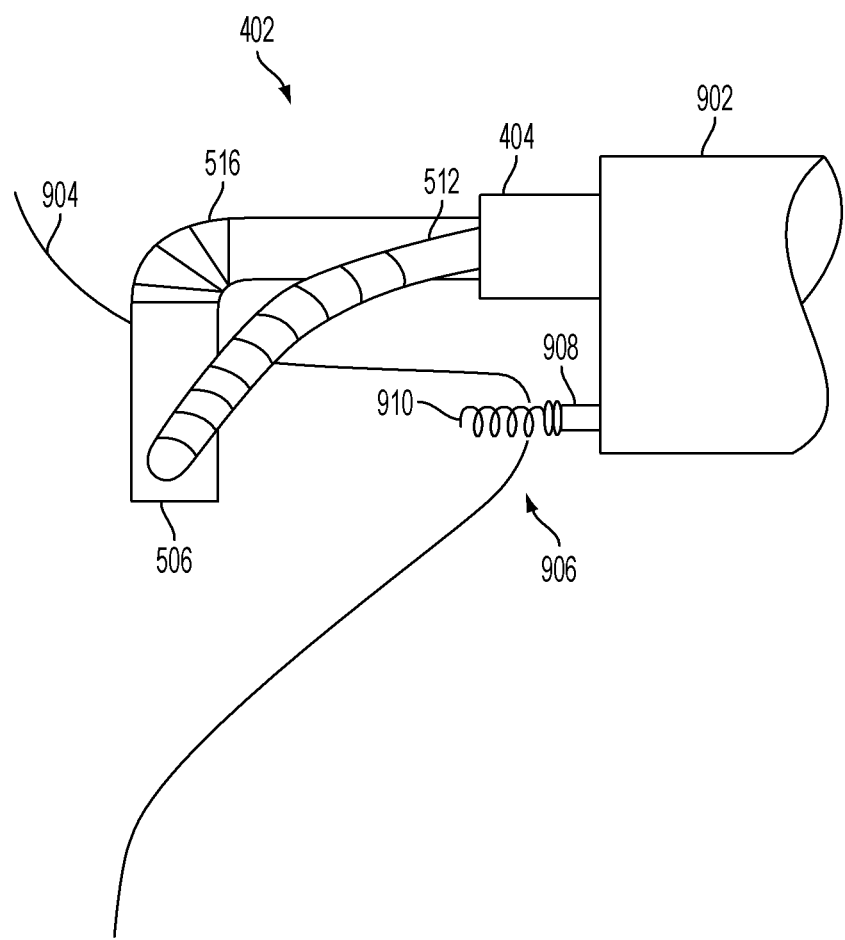
FIG. 10 is a top view of the tissue manipulation device of FIG. 8 receiving tissue between open jaw members.
Figure 11:
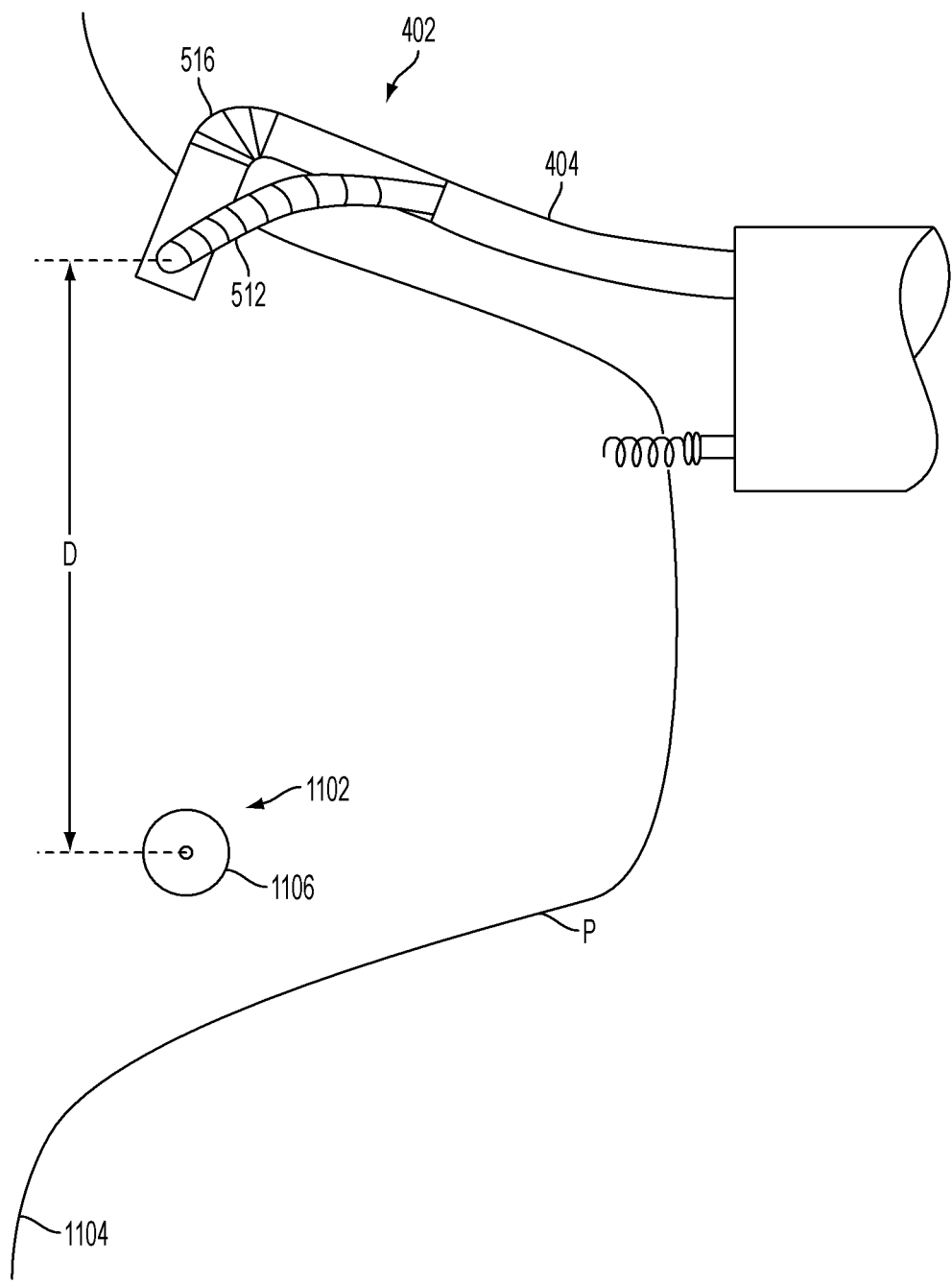
FIG. 11 is a top view of one embodiment of a tissue manipulation device applying a second fastener to form an extended tissue plication.

FIGS. 9-11 illustrate one embodiment of a method of creating and securing one or more gastric plications. The methods of the present invention are generally, though not exclusively, characterized by approaching a tissue wall along a perpendicular axis thereof, and articulating, pivoting, or positioning jaws of a tissue manipulation device so as to be parallel to the tissue surface rather than perpendicular to it. A tissue grasper can then be used to draw tissue through the jaws transversely (i.e., transversely to a longitudinal axis of the jaws) to create a gastric plication.

As described above, the various embodiments of the devices and systems disclosed herein can be utilized in a variety of procedures to treat a number of medical conditions. For example, devices as disclosed herein can be configured for use during an open surgical procedure. Alternatively, the devices and systems described herein can be configured to be passed through one or more layers of tissue during a laparoscopic or other minimally invasive procedure. Furthermore, the devices can be configured for introduction into a patient via an access port or other opening formed through one or more layers of tissue, or via a natural orifice (i.e., endoscopically).

Figure 2:
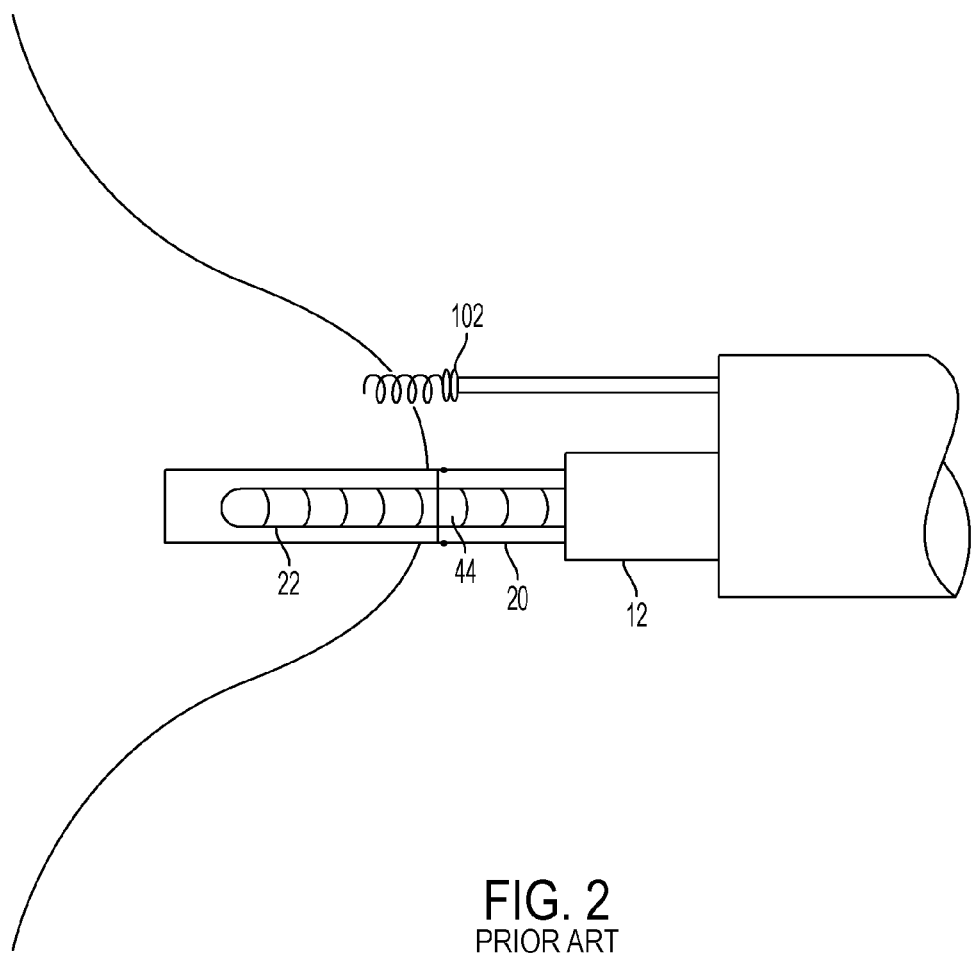
FIG. 2 is a top view of the prior art tissue manipulation device of FIG. 1A receiving tissue between open jaw members.
Figure 3:
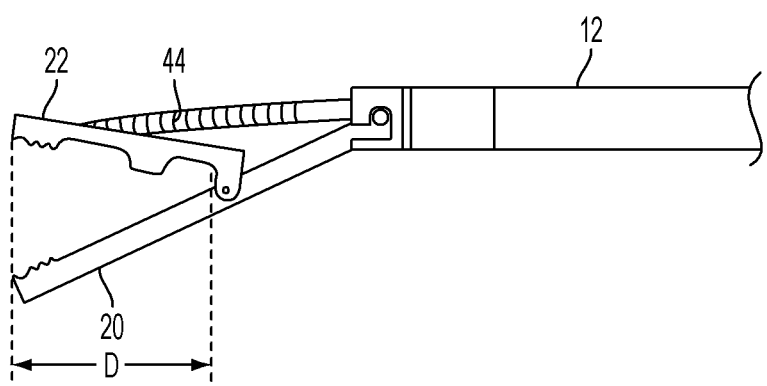
FIG. 3 is a side view of the prior art tissue manipulation device of FIG. 1A.

Regardless of how the devices are introduced into a patient's body, the method of creating a tissue plication can begin by advancing a tissue manipulation device, such as the device 402 described above, from the distal end of a transport body, such as an endoscope. The tissue manipulation device can be advanced toward a tissue wall along a perpendicular axis thereof, similar to the approach of prior art devices illustrated in FIG. 2. However, prior to engaging tissue with the first and second jaw members of the device, the device can be moved into an articulated configuration such that the first and second jaw members are substantially parallel to the tissue wall.

FIG. 9 shows one embodiment of this procedure, in which the tissue manipulation device 402 coupled to the elongate shaft 404 extends from a working channel o f a transport endoscope 902. The elongate shaft 404 can be oriented along an axis perpendicular to a tissue wall 904, and the articulation portion 516 of the tissue manipulation device 402 can be actuated to rotate first and second jaw members 504, 506 (only the second jaw member 506 is visible in the top view of FIG. 9) into an orientation substantially parallel to the tissue wall 904. Either prior to or following articulation into the position shown in FIG. 9, a fastener delivery member 512 that extends from the elongate shaft 404 and is coupled to the second jaw member 506 can be urged proximally (i.e., back into the elongate shaft 404) to cause the first and second jaw members to assume an open configuration, as shown in FIG. 5B.

In order to draw tissue between the first and second jaw members 504, 506, a separate tissue grasper 906 may be utilized in conjunction with the tissue manipulation device 402. The tissue grasper 906 can itself include an elongate shaft 908 having a tool 910 on or near a distal end of the shaft that is configured to engage tissue. The tissue grasper 906 can be configured to extend from the endoscope 902 as well, and can be configured to move independently of the tissue manipulation device 402. One skilled in the art will appreciate that such tools are generally utilized in endoluminal procedures and that several different tools may be utilized for performing a procedure endoluminally. In the illustrated embodiment, the tool 910 at the distal end of the tissue grasper 906 is a corkscrew-shaped member configured to be rotated to engage tissue. In alternative embodiments, pincers, suction devices, barbs, or other elements capable of engaging the tissue wall 904 can be employed.

As a result of the fact that the tissue grasper 906 can move independently of the tissue manipulation device 402, the tissue grasper can be deployed either before or after positioning of the tissue manipulation device. For example, in some embodiments the tissue manipulation device can be articulated into the position shown in FIG. 9, and the first and second jaw members can be urged into an open configuration by movement of the fastener delivery member 512 prior to deploying the tissue grasper 906. In such an embodiment, the tissue grasper 906 can be advanced distally through the jaw opening 518 to the position shown in FIG. 9. Alternatively, the tissue grasper 906 can be deployed first and the open jaw members can then be articulated over the tissue grasper into the illustrated configuration.

After the tissue grasper 906 has engaged the tissue wall 904, e.g., by rotating the corkscrew tool 910 while in contact with the tissue wall, the tissue grasper 906 can be retracted proximally back into the endoscope 902. As a result of the articulated configuration of the first and second jaw members, this proximal movement of the tissue grasper 906 is transverse to the plane defined by a longitudinal axis of the first and second jaw members 504, 506. Furthermore, the tissue grasper 906 can be disposed between the first and second jaw members within the jaw opening 518. Accordingly, the tissue grasper 906 can draw a portion of the tissue wall 904 through the jaw opening 518 as it moves proximally, thereby creating a fold, or plication, of tissue, as shown in FIG. 10. Drawing tissue through the open jaw members transversely, rather than into the open jaws from an open end thereof, allows the creation of a tissue plication that is deeper than the length of the first and second jaw members. Moreover, drawing tissue transversely through the jaw members can prevent undesired surrounding tissue from being unintentionally drawn between the jaws. This can be important because it can be undesirable for some surrounding tissue, such as small bowel, omentum, adjacent organs such as the liver or pancreas, and blood vessels, to be included in a gastric plication, as complications can arise such as gastric obstruction, tissue necrosis, and undetected bleeding. By drawing tissue through the open jaw members transversely, larger surrounding tissue or organs can be prevented from entering the jaw opening 518 by the sidewalls of the jaw members themselves.

Following approximation of a portion of the tissue wall 904 into a tissue plication disposed between the first and second jaw members 504, 506, the fastener delivery member 512 can be urged distally to cause the first and second jaw members to clamp down on the tissue disposed therebetween. In other words, the jaw members and fastener delivery member can be urged into the configuration shown in FIG. 5C (albeit in the articulated configuration shown in FIG. 10). The needle assembly 702 can then be advanced distally through the fastener delivery member 512 such that the needle exits the fastener delivery member, pierces through the layers of tissue disposed between the first and second jaw members 504, 506, and passes through the opening 608 formed in the first jaw member.

The actuation member 810 on the housing 708 can then be utilized to advance the anchor assembly 704 distally and ultimately eject the first distal anchor 814 from the needle opening 806. The needle assembly 702 can then be retracted within the fastener delivery member 512 and the second proximal anchor 816 can be ejected from the needle opening 806 on an opposite side of the tissue plication from the first anchor 814. Alternatively, the needle assembly 702 can be retracted and the first and second jaw members 504, 506 can be opened such that the tissue manipulation device 402 can be disengaged from the tissue wall 904. The second proximal anchor 816 can then be ejected or, in some embodiments, the procedure can be repeated at a second position and the proximal anchor can be ejected at the second position on the same side of the tissue plication as the distal anchor 814. Regardless, a suture or other flexible element remains connecting the first and second anchors 814, 816. One or more cinching elements can be advanced along the suture to draw the first and second anchors 814, 816 closer together, thereby securing the tissue plication.

The method described above can be repeated as necessary to implant a plurality of anchors and create a series of tissue plications. FIG. 11 illustrates one embodiment in which a first anchor assembly 1102 has been implanted to form a tissue plication P from a portion of a tissue wall 1104. Given the top-view orientation of the figure, only a proximal anchor 1106 of the anchor assembly 1102 is visible, as the distal anchor is below the tissue plication P.

Also shown in FIG. 11 is the tissue manipulation device 402 applying a second anchor assembly at a second location a distance D apart from the position of the first anchor assembly 1102. As shown in the figure, by applying a series of anchors in a line along the tissue wall 1104, the tissue plication P can be extended to any length. While the distance D can be chosen according to the type of tissue and degree of fastening required, in some embodiments, the distance D between adjacent anchor assemblies can be 2 cm or less. If basket anchors are used, the distance D between adjacent anchor assemblies can be 3 cm or less. In other embodiments, the distance between anchors can be selected based on a variety of factors including, for example, the size and type of the anchors used, as well as the thickness of the tissue. FIG. 11 also illustrates the natural deflection that can occur along the length of the elongate shaft 404 due to forces being exerted during actuation of the various components of the tissue manipulation device 402 (e.g., actuation of the fastener delivery member 512, articulating portion 516, delivery of an anchor assembly, etc.).

The method of extending a tissue plication shown in FIG. 11 can be repeated to create a single line of anchors along a plication, or multiple lines of anchors securing a plication. Multiple lines of anchors can be formed along a plication by drawing the tissue through the first and second jaw members 504, 506 to different depths. This method can be used, for example, to create a very deep tissue plication. In one embodiment, a first line of anchors can be deployed to create a tissue plication of a first depth, and then a second line of anchors can be deployed by drawing the plication through the first and second jaw members beyond the position of the first line of anchors to extend the depth of the tissue plication.

Figure 12:
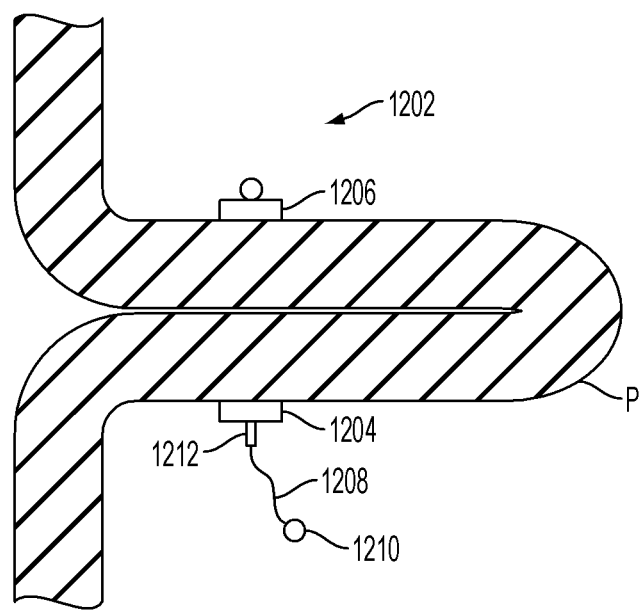
FIG. 12 is a side cross-sectional view of one embodiment of a serosa-to-serosa tissue fold secured with a fastener.

FIG. 12 illustrates a cross-sectional view of the tissue plication P, showing a single anchor assembly 1202 securing the plication. A first distal anchor 1204 is visible on one side of the tissue plication P, and a second proximal anchor 1206 is visible on an opposite side of the plication. As noted above, in some embodiments both anchors can be positioned on a same side of the tissue plication with a suture or other connecting element extending through the tissue and between the anchors. The two anchors 1204, 1206 can be connected by a suture or flexible element 1208 that, in some embodiments, can have a terminal end that is a loop 1210. The suture 1208 can be formed from a variety of materials such as monofilament, multifilament, or any other conventional suture material, elastic or elastomeric materials, e.g., rubber, etc. Disposed along the length of the suture 1208 can be one or more locking or cinching mechanisms 1212 that provide for movement of an anchor along the suture in a first direction and preferably lock, inhibit, or prevent the reverse movement of the anchor back along the suture.

One skilled in the art will appreciate that the methods described above can be adapted for use with approach angles that are either exactly perpendicular to a tissue wall, substantially perpendicular, or at any other angle to the tissue wall. The general principle remains that the tissue engaging jaw members of the device can be articulated to any required degree such that they assume a position substantially parallel to the tissue wall.

Figure 13A:
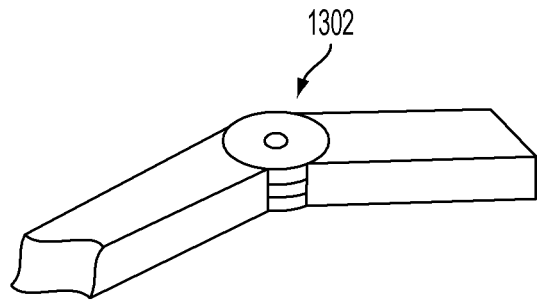
FIG. 13A is a perspective view of one embodiment of an articulating portion of a tissue manipulation device.
Figure 13B:
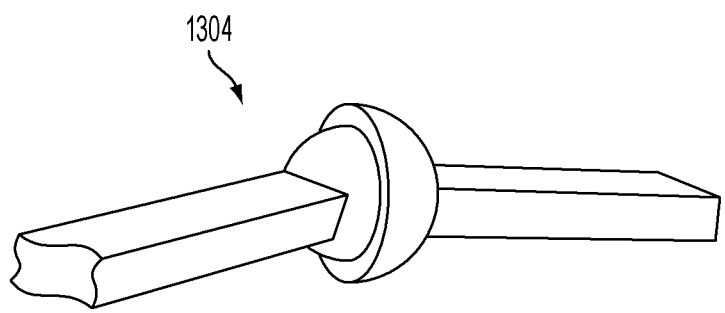
FIG. 13B is a perspective view of another embodiment of an articulating portion of a tissue manipulation device.
Figure 13C:
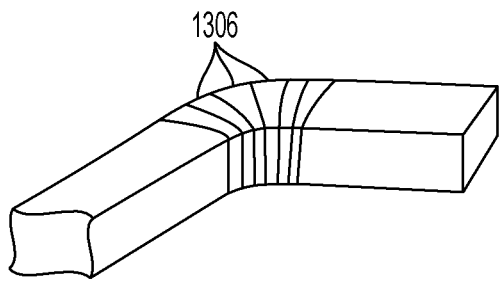
FIG. 13C is a perspective view of still another embodiment of an articulating portion of a tissue manipulation device.

FIGS. 13A-13C illustrate exemplary embodiments of an articulating portion that can be employed in a tissue manipulation device to provide various ranges of motion. For example, an articulating portion can be formed as a hinge 1302 that allows two-dimensional rotational movement, as shown in FIG. 13A. Alternatively, freedom of movement can be accomplished by using a ball-and-socket joint 1304 as an articulating portion, as shown in FIG. 13B. In another embodiment shown in FIG. 13C, an articulating portion can be created by connecting a plurality of jointed segments 1306. Each segment 1306 can move in a certain range of motion with respect to each adjacent segment. The cumulative effect of each of the segments 1304 can provide a large range of motion for the articulating portion. In some embodiments, a similar strategy can be used to connect multiple ball-and-socket joints to produce a greater cumulative range of motion. Still further, use of ball-and-socket joints or jointed segments can allow the articulating portion to move in three dimensions, not simply pivot within a particular plane, as with the hinge of FIG. 13A.

Figure 14:
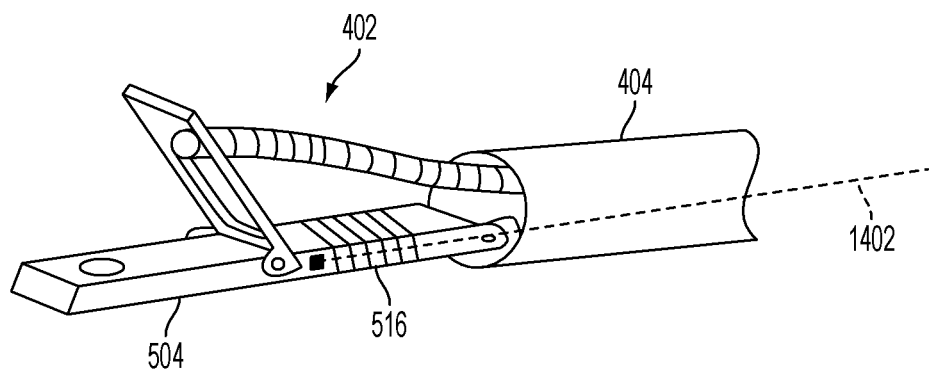
FIG. 14 is a perspective view of one embodiment of a tissue manipulation device having an articulation actuating member.

The articulating portion can be actuated in a variety of manners. FIG. 14 illustrates one exemplary embodiment in which an articulation actuating member 1402 in the form of a wire is coupled to the first jaw member 504 at a location distal to the articulating portion 516. In some embodiments, the articulation actuating member 1402 can be coupled to the first jaw member 504 on a sidewall thereof, such that tensioning the articulation actuating member can actuate the articulation portion 516 and cause the first and second jaw members to move from the straight configuration shown in FIG. 14 to the articulated configuration shown in FIG. 6C. There are a variety of articulation actuating members available, all of which are within the scope of the invention. For example, in some embodiments the articulation actuating member can include one or more connecting members, which can include cables, ribbons, bands, etc. In other exemplary embodiments the articulation actuating member can include any mechanically, electrically, pneumatically, or hydraulically powered actuators that can be incorporated into the tissue manipulation device 402. In some embodiments, other actuators, such as springs, shape memory alloys, and other mechanical linkages can also be used. In other embodiments, the articulation actuation member can be incorporated into the fastener delivery member 512 such that movement of the fastener delivery member can both open and close the first and second jaw members, and effect articulation of the device between a straight and articulated configuration. Furthermore, one or more actuating members can also be included on other surfaces (e.g., an opposing sidewall from that shown in FIG. 14) to either recover from an articulated configuration (e.g., for removal from a patient's body) or to allow for articulation in more than one direction.

Figure 15:
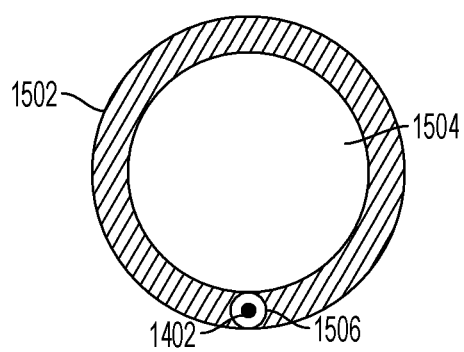
FIG. 15 is a cross-sectional view of one embodiment of a sleeve housing an articulation actuating member.

The one or more articulation actuating members 1402 can be coupled to the tissue manipulation device 402 in any manner known in the art. Moreover, in some embodiments, the articulation actuating members 1402 can be coated or covered to protect from catching or otherwise damaging surrounding tissue during use. FIG. 15 illustrates one embodiment of a sheath 1502 that can be disposed around any of the elongate shaft 404, first jaw member 504, and fastener delivery member 512. The sheath 1502 can include an inner lumen 1504 to house one or more components of the tissue manipulation device 402, and also includes one or more sub-lumens 1506 formed in a sidewall thereof to house the wire articulation actuating member 1402.

Furthermore, and although not shown in the attached figures, any of the exterior components of the tissue manipulation device 402 or surgical instrument 400 can be covered, coated, or can contain additional features or geometry to minimize the risk of unintentional tissue damage during insertion, operation, or removal. Exemplary features include blunt surfaces, tapered tips, fillets, chamfers, elastomeric coatings/coverings, or any other similar feature known to one skilled in the art.

The methods disclosed above demonstrate the use of a device of the present invention to create and secure a gastric plication. The devices and systems of the present invention can be utilized with a variety of methods of plication placement within the gastric cavity. For example, some data has shown that reduction of gastric volume through invagination of the greater curvature of the stomach has yielded significantly larger excess weight loss percentage than invagination of the lesser curvature. Exemplary methods of plication formation and placement on the anterior and posterior surfaces of the gastric cavity are disclosed in U.S. application Ser. No. 13/326,625 to Felder et al., the contents of which are hereby incorporated by reference in their entirety.

Figure 16A:
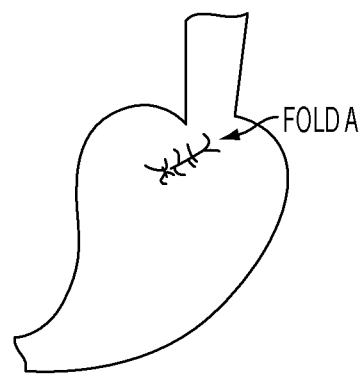
FIG. 16A illustrates an exemplary plication positioned in the upper region of the gastric cavity.
Figure 16B:
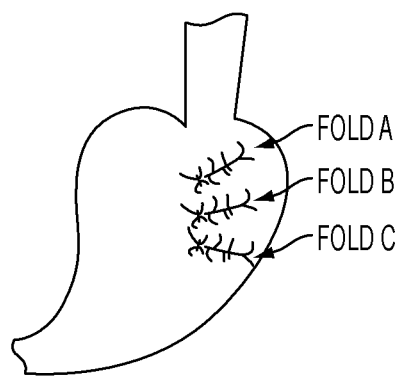
FIG. 16B illustrates an exemplary method of forming multiple plications by fanning out from the position of the plication shown in FIG. 16A.

By way of example, in an exemplary method, one or more gastric plications can be formed on an anterior or posterior wall of the greater curvature of the stomach. One embodiment of an exemplary method for forming plications is illustrated in FIGS. 16A and 16B. As shown in FIG. 16A, a device as disclosed herein can be inserted through a patient's esophagus and into the stomach cavity. The device can then be positioned and/or articulated to access the anterior or posterior wall of the stomach near or within the fundus. Finally, a plication can be created and secured using, for example, the method described above. This leaves a secured gastric plication, as shown by "Fold A" of FIG. 16A.

To create additional plications, the surgical device can be moved from the position of "Fold A" shown in FIG. 16A to a second position labeled "Fold B" in FIG. 16B. The above process can then be repeated to create and secure a second plication. If necessary, the surgical device can again be moved from the position of "Fold B" to a third position labeled "Fold C." Additional folds can be made as necessary, forming a fan-shaped pattern. After forming and securing all plications, the surgical device can be retracted back out of the gastric cavity through the esophagus, leaving only the secured plications.

The multiple plications discussed above can be formed in a clockwise or counterclockwise direction (i.e., moving from Fold A to Fold C, or Fold C to Fold A). In addition, plications can be formed on both the anterior and posterior walls of the greater curvature of the stomach. In forming plications on both walls, the methods of the present invention can include forming all plications on one wall before the other, or alternating between the two. In addition, plications can be formed on both walls in a particular section of the stomach before alternately or otherwise forming plications in other sections of the stomach. Further, plications can be formed in any of a proximal or a distal direction. For example, plications can be formed on both the posterior and anterior walls in or near the fundus before forming plications on alternate walls in a distal to proximal direction in other areas of the stomach. Still further, the respective folds created on the anterior and posterior walls of the stomach need not be attached to each other. These methods can provide the benefit of limiting the impact of a decreasing working space as the multiple plications are formed and secured.

Figure 17A:
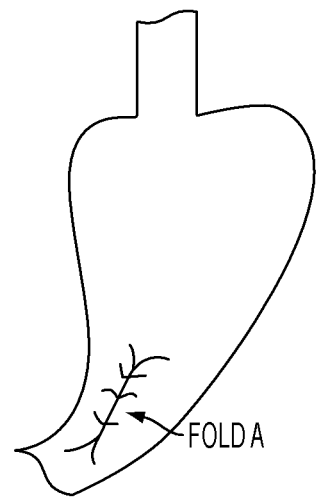
FIG. 17A illustrates an exemplary plication created in the lower region of the gastric cavity.

In another embodiment, multiple plications can be formed in an end-to-end fashion to create a single extended plication, rather than the fan-shaped pattern described above. To do so, a surgical device according to the teachings of the invention can be inserted into a patient's stomach through the esophagus. Once in the stomach, the surgical device can be positioned along the anterior wall of the stomach near or within the antrum, as shown in FIG. 17A. The surgical device can be utilized according to any of the methods described above to form and secure a first gastric plication labeled "Fold A" in FIG. 17A.

Figure 17B:
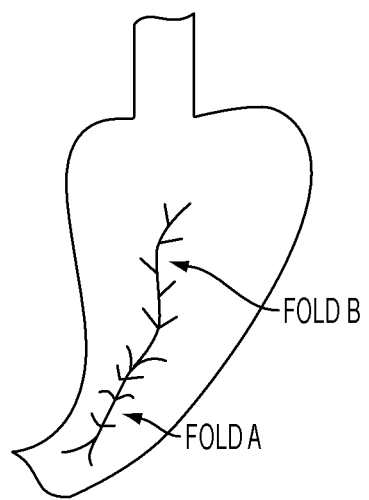
FIG. 17B illustrates an exemplary method of forming a second plication by extending from an end point of the plication shown in FIG. 17A.

Following formation of the first plication, the surgical device can be retracted toward the esophagus. Once the surgical device is in a position to create a gastric plication that extends from the first gastric plication (labeled "Fold A"), the surgical device can be actuated to create a second gastric plication labeled "Fold B" in FIG. 17B.

Figure 17C:
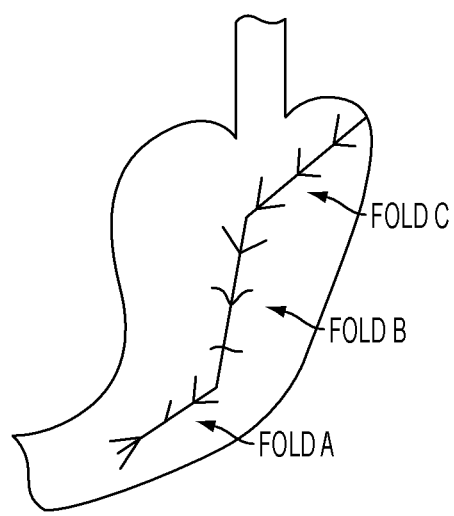
FIG. 17C illustrates an exemplary method of forming a third plication off the plications shown in FIG. 17B.

The above process can be repeated again to create a third gastric plication (labeled "Fold C"), as shown in FIG. 17C. Depending on the size (e.g., length) of the jaw members of the surgical device, the process may be repeated more or fewer times in order to create a desired number of gastric plications.

Figure 18:
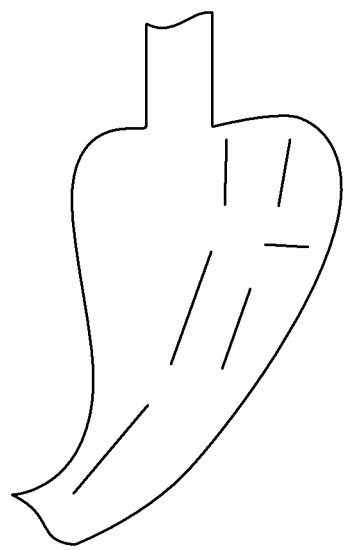
FIG. 18 illustrates an exemplary combination of the various plication patterns shown in FIGS. 16A-17C.

Similarly to the methods of forming plications in a fan-shaped pattern described above, the above methods contemplate forming all plications on an anterior wall of the stomach followed by forming all plications on a posterior wall, or alternately forming plications on the anterior wall and the posterior wall. Further, plications may be formed in both walls of one section of a cavity before forming plications alternately or in another manner in another section of the cavity. In addition, the plications formed on the anterior wall need not be attached to those on the posterior wall of the stomach. Still further, the plications can be formed in a distal to proximal order, as shown in the figures, or in a proximal to distal order (i.e., moving from Fold C to Fold A). Following the formation of the final plication, the surgical device can be removed from the stomach via the esophagus. One skilled in the art will appreciate that a combination of the embodiments described above may be used (e.g., first forming a plication in or near the fundus, and then forming a plication in a distal to proximal order, or first forming at least one plication in the form of a fan and then forming at least one plication in the form of a line), as shown in FIG. 18. There are a number of variations in the order and direction in which plications can be formed in the cavity, all of which are considered within the scope of the present invention.

The devices disclosed herein can be designed to be disposed after a single use, or they can be designed for multiple uses. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

For example, the devices disclosed herein may be disassembled partially or completely. In particular, and by way of example only, the first and second jaw members of the tissue manipulation device may be decoupled from the elongate shaft and fastener delivery member. Furthermore, any fastener deployment assembly may be removed from the fastener delivery member and replaced or cleaned and reloaded. The first and second jaw members themselves may also be decoupled and cleaned or replaced prior to reassembly. The articulating portion may also be disassembled and cleaned or replaced. One skilled in the art will appreciate that every component of the devices described herein can be disassembled and cleaned or replaced prior to reassembling the device.

Preferably, the devices described herein will be processed before surgery. First, a new or used instrument can be obtained and, if necessary, cleaned. The instrument can then be sterilized. In one sterilization technique, the instrument is placed in a closed and sealed container, such as a plastic or TYVEK® bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. In many embodiments, it is preferred that the device is sterilized. This can be done by any number of ways known to those skilled in the art including beta or gamma radiation, ethylene oxide, steam, and a liquid bath (e.g., cold soak).

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A method of acquiring and fixating tissue, comprising:
    inserting into a body lumen a tissue grasper, an elongate shaft, and an end effector coupled to the elongate shaft, wherein the end effector has a first jaw that pivots relative to a second jaw in a first plane and about an axis that extends through a proximal end of the first jaw and a portion of the second jaw;
    pivoting the first and second jaws in a direction transverse to the first plane such that the first and second jaws move from a first configuration, in which a longitudinal axis of the elongate shaft lies in the first plane, to a second configuration, in which the longitudinal axis of the elongate shaft is transverse to the first plane;
    positioning the tissue grasper to engage tissue;
    drawing the tissue through the first and second jaws by moving the tissue grasper transversely with respect to the first plane when the first and second jaws are in the second configuration; and
    delivering a fastener through the tissue disposed between the first and second jaws from a fastener delivery member coupled to the second jaw;
    wherein the first plane is defined by proximal and distal ends of each of the first and second jaws in both the first configuration and the second configuration.

2. The method of claim 1, wherein inserting the end effector and elongate shaft into the body lumen comprises positioning the elongate shaft perpendicular to an inner surface of the body lumen, and pivoting the first and second jaws in the direction transverse to the first plane comprises positioning the first and second jaws such that a longitudinal axis of any of the first and second jaws is parallel to the inner surface of the body lumen.

3. The method of claim 1, wherein moving the tissue grasper transversely with respect to the first plane comprises moving the tissue grasper perpendicular to a longitudinal axis of any of the first and second jaws.

4. The method of claim 1, wherein pivoting the first and second jaws in the direction transverse to the first plane includes translating an articulation actuating member parallel to the longitudinal axis of the elongate shaft.

5. The method of claim 1, wherein delivering the fastener includes moving the fastener delivery member from a low-profile delivery configuration in which the fastener delivery member is positioned substantially within a channel formed in the second jaw to an open configuration in which a distal portion of the fastener delivery member is positioned substantially outside of the channel.

6. The method of claim 5, wherein delivering the fastener further includes extending a needle from the fastener delivery member such that the needle passes through openings formed in the first and second jaws, as well as through the tissue disposed therebetween.

7. A method of acquiring and fixating tissue, comprising:
    positioning an end effector coupled to a distal end of an elongate shaft at a surgical site in a first configuration such that a longitudinal axis of the elongate shaft lies in a first plane, the end effector having a first jaw that pivots relative to a second jaw about an axis that extends through a proximal end of the first jaw and a portion of the second jaw;
    articulating the end effector relative to the elongate shaft in a direction transverse to the first plane such that the end effector moves to a second configuration in which the first plane is transverse to the longitudinal axis of the elongate shaft; and
    drawing tissue through the first and second jaws in a direction transverse to the first plane;
    wherein the first plane is defined by lengths of the first and second jaws in both the first configuration and the second configuration.

8. The method of claim 7, wherein drawing the tissue through the first and second jaws includes engaging the tissue with a tissue grasper capable of moving independently from the end effector.

9. The method of claim 7, wherein the end effector is positioned such that the first plane is transverse to a tissue surface prior to articulation of the end effector and is parallel to the tissue surface after articulation of the end effector.

10. The method of claim 7, further comprising delivering a fastener through the tissue disposed between the first and second jaws.

11. The method of claim 10, wherein the fastener is delivered through a flexible fastener delivery member that extends from the elongate shaft and is coupled to the second jaw.

12. The method of claim 11, wherein delivering the fastener includes extending a needle from the flexible fastener delivery member such that the needle passes through openings formed in the first and second jaws, as well as through the tissue disposed therebetween.

13. A method for acquiring and fixating tissue, comprising:
    inserting into a body lumen an end effector having first and second jaws that are pivotally coupled to one another, the end effector being coupled to an elongate shaft and arranged in a first configuration such that a longitudinal axis of the elongate shaft lies in a first plane;

approaching a tissue surface such that the first plane and the longitudinal axis of the elongate shaft are transverse to the tissue surface;

articulating the end effector relative to the elongate shaft about a pivot point located proximal to a location of pivotal coupling between the first and second jaws in a direction transverse to the first plane such that the end effector moves to a second configuration in which the first plane is substantially parallel to the tissue surface and transverse to the longitudinal axis of the elongate shaft;

drawing tissue through the first and second jaws using a tissue grasper that can move independently from the end effector; and delivering a fastener through the tissue disposed between the first and second jaws;

wherein the first plane is defined by relative movement of the first and second jaws in both the first configuration and the second configuration.

14. The method of claim 13, wherein delivering the fastener includes moving a fastener delivery member from a low-profile delivery configuration in which the fastener delivery member is positioned substantially within a channel formed in the second jaw to an open configuration in which a distal portion of the fastener delivery member is positioned substantially outside of the channel.

15. The method of claim 14, wherein delivering the fastener further includes extending a needle from the fastener delivery member such that the needle passes through openings formed in the first and second jaws, as well as through the tissue disposed therebetween.

* * * * *